United States Patent [19]

Warnicki et al.

[11] Patent Number: 4,995,716

[45] Date of Patent: Feb. 26, 1991

[54] METHOD AND APPARATUS FOR OBTAINING THE TOPOGRAPHY OF AN OBJECT

[75] Inventors: Joseph W. Warnicki, Pittsburgh; Paul G. Rehkopf, Murrysville, both of Pa.; James L. Cambier, Rome; Salvins J. Strods, Waterville, both of N.Y.

[73] Assignee: Par Technology Corporation, New Hartford, N.Y.

[21] Appl. No.: 321,252

[22] Filed: Mar. 9, 1989

[51] Int. Cl.[5] ............................................... A61B 2/10
[52] U.S. Cl. .................................... 351/212; 351/247
[58] Field of Search ................ 351/212, 247; 356/395, 356/396

[56] References Cited

U.S. PATENT DOCUMENTS 3,169,459  2/1965  Friedberg ..................... 351/212 X
4,685,140  8/1987  Mount .......................... 351/212 X

OTHER PUBLICATIONS

Joseph W. Warnicki, Paul G. Rehkopf, Diane Y. Curtin, Stephen A. Burns, Robert C. Arffa, and John C. Stuart, "Corneal Topography Using Computer Analyzed Rasterstereographic Images," in *Applied Optics*, vol. 27, No. 6, (Mar. 15, 1988), pp. 1135–1140.

Thomas Olsen, "On the Calculation of Power from Curvature of the Cornea," *British Journal of Ophthalmology*, (1986), vol. 70, pp. 152–154.

Carsten Edmund and Erik Sjontoft, "The Central-Peripheral Radius of the Normal Corneal Curvature,"*Acta Ophthalmologica*, (1985), vol. 63, pp. 670–677.

Joseph W. Warnicki and Paul G. Rehkopf, "Development of an Imaging System for Ophthalmic Photography," *Journal of Biological Photography*, vol. 53, No. 1, (Jan. 1985), pp. 9–18.

Stephen P. Klyce, "Computer-Assisted Corneal Topography," *Investigative Opthalmology and Visual Science*, vol. 25, (1984), pp. 1426–1435.

Marco S. Caceci and William P. Cacheris, "Fitting Curves to Data," *Byte*, (May, 1984), pp. 340–357.

J. James Rowsey, M.D., A. E. Reynolds, Ph.D., Randy Brown, "Corneal Topography," *Arch Ophthalmol*, vol. 99, (Jun. 1981), pp. 1093–1100.

M. S. Moreland, M.D., C. A. Barce, B.A., M. H. Pope, Ph.D., "Moire Topography in Scoliosis: Pattern Recognition and Analysis," *Moire Fringe Topography and Spinal Deformity*, Pergamon Press, (1981), pp. 171–185.

Marius C. VanWijk, "Accuracy of Moire Topography," *Moire Fringe Topography Spinal Deformity*, Pergamon Press, (1981).

J. D. Doss et al., "Method for Calculation of Corneal Profile and Power Distribution", *Arch Ophthalmol*, 1261 (1981).

T. Yatagai, M. Idesawa, H. Ohshima, and M. Suzuki, "Automatic Measurement of 3-D Shapes Using Scanning Moire Method, " *Moire Fringe Topography*, pp. 249–257.

(List continued on next page.)

Primary Examiner—Rodney B. Bovernick
Attorney, Agent, or Firm—Arnold B. Silverman; Suzanne Kikel

[57] ABSTRACT

A system, method, and apparatus for obtaining the corneal topography of an object using computer analyzed rasterstereographic images. The object may be nontransparent and diffusing, or it may be transparent and nondiffusing, such as a cornea. Rasterstereographic images of a cornea are produced by staining the cornea with a fluorescein solution which projects a light and dark line pattern onto the cornea through a grid. When obtaining the topography of a cornea, several different filters are used for producing and obtaining a grid image. An image processor uses unique software to store and analyze data extracted from the grid pattern. A video camera, an illuminator, the filters, and the grid may be mounted on a microscope.

50 Claims, 10 Drawing Sheets

OTHER PUBLICATIONS

E. Hierholzer and W. Frobin, "Rasterstereographic Measurement and Curvature Analysis of the Body Surface of Patients with Spinal Deformities", *Moire Fringe Topography*, pp. 267–276.

N. Ikeda, "Perspective Correction of the Moire Photograph," *Journal of the Biological Photographic Association*, vol. 47, No. 3, (Jul., 1979), pp. 107–110.

M. S. Karlan, M.C., M. Madden, M.A., and M. B. Habal, M.D., "Biostereometric Analysis in Plastic and Reconstructive Surgery," *Plastic and Reconstructive Surgery*, vol. 62, No. 2 (Aug., 1978), pp. 235–239.

T. W. Smith, M.D., "Corneal Topography," Documenta Opthalmologica 43.2 (1977), pp. 249–276.

S. Wittenberg and Wm. M. Ludlam, "Planar Reflected Imagery in Photokeratoscopy," *Journal of the Optical Society of America*, vol. 60, No. 7, (Jul., 1970), pp. 981–985.

H. Takasaki, "Moire Topography," *Applied Optics*, vol. 9, No. 6, (Jun., 1970), pp. 1467–1472.

Wm. M. Ludlam and S. Wittenberg, "Measurements of the Ocular Dioptric Elements Utilizing Photographic Methods," *American Journal of Optometry Publishing Association*, (Apr., 1966), pp. 249–267.

S. Wittenberg and Wm. W. Ludlam, "Derivation of a System for Analyzing the Corneal Surface from Photokeratoscopic Data," *Journal of the Optical Society of America*, vol. 56, No. 11, (Nov., 1966), pp. 1612–1615.

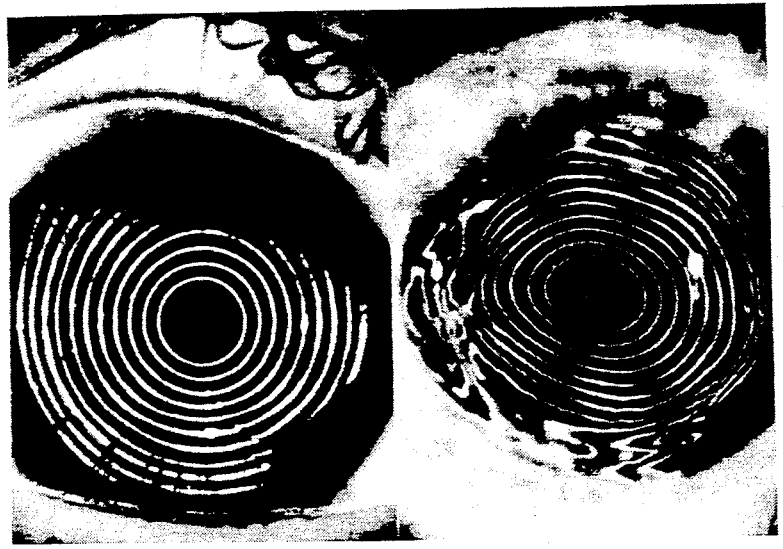
PRIOR ART
FIG. 1a
PRIOR ART
FIG. 1b
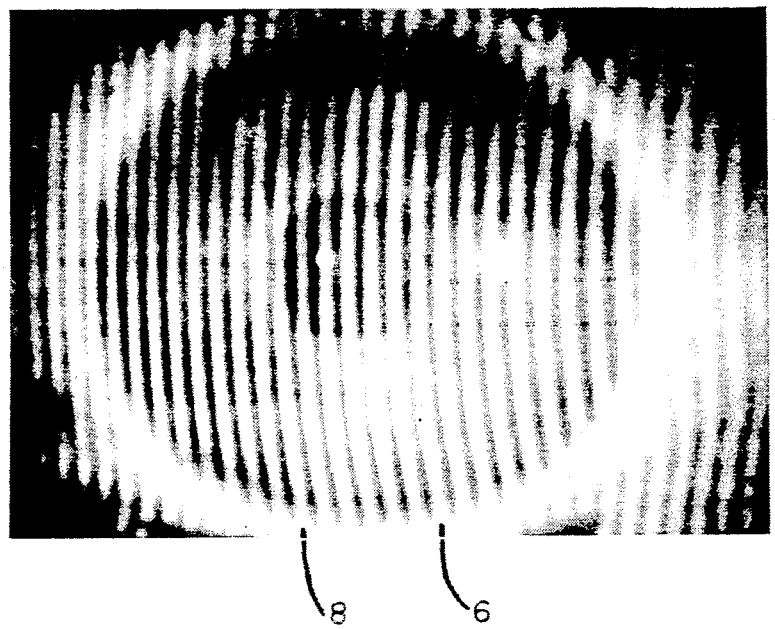
FIG. 2

FIG_9

METHOD AND APPARATUS FOR OBTAINING THE TOPOGRAPHY OF AN OBJECT

BACKGROUND OF THE INVENTION

1. Field of the Invention

This present invention relates to a system, method, and associated apparatus for enabling the use of rasterstereographical principles for determining the curvature and surface detail across the surface of an object by using a computer analyzed rasterstereographic technique. More specifically, a projected light and dark pattern on the object is picked up by a video camera and the image is digitized by an image processor which calculates the surface detail by evaluating the distortion of the grid lines.

2. Description of the Prior Art

In recent years there has been increased interest in both qualitative and quantitative measurements of an object by topography. Particularly this increased interest has been in regard to corneal topography especially relating to keratorefractive procedures. Since keratorefractive procedures correct the refractive error of the eye by altering the curvature of the corneal surface, topographic measurements of the corneal curvature are important in planning, performing, and assessing the effect of these procedures.

Corneal topography has been proven of value for numerous uses including predicting the result of radial keralotomy, evaluating the design of epikeratophakia for myopia, diagnosis and staging of keratoconus, and guiding suture removal after corneal transplantation.

There have been previously reported photographic methods based on the keratoscopic disk system. (See "Corneal Topography," J. J. Rowsey, et al., Arch. Ophthalmol., Vol. 99, 1093 [1981]). This keratoscopic system consists of a series of black and white concentric rings on a circular disk. When this disk is placed in front of the eye, the rings are reflected by the corneal surface and their position, size, and spacing in the reflected image are determined by the corneal shape.

Current commercial systems utilizing illuminated concentric circular rings surrounding a viewing port through which photographs are taken have been known. If the cornea is spherical, the rings appear round and regularly spaced. If the cornea is oval or astigmatic, the rings are oval and the spacing varies in different axes. This is known as the placido disk technique.

These techniques, while providing a visual representation of the corneal surface, do not provide quantitative information. Computer programs have been developed which calculate the corneal profile and the optical power distribution on the corneal surface from placido disk images. See "Method for Calculation of Corneal Profile and Power Distribution," J. D. Ross, et al., Arch Ophthalmol., 1261 (1981).

Computer analyzing techniques have been developed for deriving quantitative information about the corneal shape from keratoscope photographs and displaying the results both numerically and graphically in easily understood forms. See "Computer-Assisted Corneal Topography, High Resolution Graphic Presentation and Analysis of Keratoscopy," S. D. Klyce, et al., Investigative Ophthalmology and Visual Science, Vol. 25, 1426 (1984).

Placido disk techniques for recording and quantifying the corneal surface have inherent limitations which reduce their clinical usefulness.

There are three main factors which limit the usefulness of the placido disk system. These factors are as follows: (1) The most central portion of the cornea is not imaged. This is due in part to the fact that there is a hole in the central portion of the placido disk through which the optical system for this technique views the cornea. This viewing port is devoid of any lighted spots or rings, and therefore there can be no reflected images on the cornea in this area. (2) The diameter of the placido disk determines how much of the corneal surface is covered by the reflected images. The smaller the diameter, the smaller the area of the cornea. The larger the diameter, the larger the area of the cornea that will be covered extending more toward the limbus or periphery of the cornea. (3) The distance between the cornea and the placido disk system also determines how much of the cornea is covered. The farther away the disk is from the cornea, the less the corneal coverage will be. The closer the disk is to the cornea, the greater the corneal coverage will be.

Other limitations of the placido disk techniques are that they do not extend to the corneal limbus due in part to shadows being cast from the eye lashes, brow and nose of the patient, nor do they work on corneas which do not have the necessary qualities to reflect an image of the disk due to conditions such as epithelial defects, scarring, or highly irregular shape.

Current computer methods being used to obtain quantitative measurements have been known to utilize photographic images acquired with the commercially available placido disk keratoscopes and are, therefore, subject to the same limitations discussed hereinbefore. In some such systems the data are entered into the computer by hand digitizing from these photographs, requiring a considerable amount of time, and the possible introduction of error during the digitization process.

While hand digitizing with some manually manipulated device is still being practiced, there is also known at least two systems for direct digitizing purposes, which systems have imaging cameras attached to the optics which, in turn, view through the central portion of the placido disk. These images are then taken directly into the computer for manipulation in calculating the corneal curvature and for determining the diopter powers.

These systems with direct digitization are still subject to the same problems as the placido disk systems having hand digitization. Although several attempts have been made to extend farther out into the limbus or periphery of the cornea, none of these systems have achieved this capability. These systems still inadequately handle corneas with very steep curvature or with a highly irregular surface.

It has been known to employ a rasterstereography method for measuring large body surfaces, curvature of the back, and reconstructive plastic surgery. Rasterstereography is an intermediate between stereography and moire topography and is a method of obtaining contour or topographic information where one of the cameras in a stereogrammetric pair is replaced with a light source which projects a grid of vertical parallel lines onto a subject.

One type of rasterstereographic system employs an electronic camera with a linear sensor, an x-y translator for image shifting, and a light source or projector. The camera and translator are connected to an on-line computer which produces an image scan of the large surface. See "Rasterstereographic Measurement and Curvature Analysis of the Body Surface," E. Hierholzer, et al., Biol. Photogr., Vol. 51, 11 (Jan. 1, 1983).

It has been known to employ a Rhonchi ruling in moire technique, which is normally a technique used for measuring the topography of a solid, nontransparent object. In moire topography a light source illuminates the Rhonchi ruling to cast shadows on the object to be measured. These shadows and the lines of Rhonchi ruling when viewed by either the eye or a camera interfere to produce contour lines of the object. See "Biostereometric Analysis in Plastic and Reconstructive Surgery," M. S. Karlan, et al., Plastic and Reconstructive Surgery, Vol. 62, (1978).

It has been known to attempt to determine corneal topography including moire techniques. A drawback is the low reflectivity of the cornea in that the cornea is a transparent, nondiffusing member, which does not allow for a good image of the grid to be formed on it.

It has been known to employ a microscope with a reticule referred to as a toposcope which uses the moire technique. A recticule is a grid or scale that is a standard piece of equipment in the moire technique. A series of straight parallel lines is imaged on the object. In the eyepiece of the microscope there is a reticule with the same number of lines. The two patterns interfere to produce the contours This instrument has been used to analyze contact lenses, but there is no evidence of using it to determine the contour of an eye. A drawback would be the low reflectivity of the cornea.

It has been known to use a fluorescein solution on a the eye, and a contact lens to determine the topography of a cornea. The fluorescein solution is placed on the eye followed by the placement of a contact lens. Blue-violet radiation produces a fluorescence pattern which gives an indication of the variable clearance between the known surface of the contact lens and the unknown cornea. For the measurements to be valid, the lens must be kept stationary, and in practice, diagnostic contact lenses are used to verify 'K' readings in conjunction with refractive findings. See "Corneal Topography," T. W. Smith, M.D., Documenta Opthalmologica 43.2, pg. 262 (1977).

It has been known to determine corneal topography by stereographic techniques, in addition to holographic interferometric, and profile techniques See "Corneal Topography," pg. 263 cited in the preceding paragraph.

As the cornea is a transparent member which is nondiffusing to light, a grid projected onto the cornea is not visible unless a diffusing material is used to provide a surface on which an image can be visualized. It has been known to spray talcum powder on anesthetized corneas to obtain stereo photographs of the cornea.

Stereophotography is traditionally used to obtain the topography of a solid, nontransparent light diffusing object that has some texture. Stereophotography may utilize two cameras which view an object of interest from two different angles relative to a fixed center line between them. Stereophotography can also be accomplished by taking two sequential images with one camera. This is accomplished by focusing the camera on a fixed point and taking an exposure. The camera is then moved laterally a fixed distance, again focusing on the same point previously used in the first image and another exposure is made.

The two stereo photos are analyzed and one of the images is chosen as a reference image. Some object of interest is chosen and the displacement of the object in the opposite stereo image can be measured. From this displacement and the angle between the two shots, an elevation of an object can be calculated.

As the stereophotography method is used on solid objects, it has not been known to adequately obtain the topography of a cornea in that sufficient topographic detail of the cornea cannot be extracted.

It has been known to use an image processing system with a video camera, flash unit, and computer and display units in the field of opthalmology where the eye images are handled electronically. However, most of the study in the ophthalmology field has been in evaluating the optic nerve, retina, and corneal surface defects, and not for determining the curvature and related topographic details of the cornea. See "Development of An Imaging System for Ophthalmic Photography," J. W. Warnicki, et al., J. Biol. Photog. 53, 9 (1985).

In the holographic interferometric technique, it is known to use a beam splitter to direct the laser beam in one direction toward a camera and in the other direction toward an object. See "Corneal Topography," pg. 264 cited hereinbefore.

In spite of these known systems, methods, and instruments, there remains a very real and substantial need for a system, method, and device which more accurately and quickly determine quantitatively and qualitatively the contour of both a light diffusing, nontransparent object and a light nondiffusing, transparent object, such as a cornea.

SUMMARY OF THE INVENTION

The present invention has met the above-described needs. A system, a method, and an apparatus of the present invention provide more accurate and easily obtainable means for determining the topography of an object particularly that of a cornea as defined hereinafter.

The apparatus may provide a support means with built-in optical means and a beam splitter along a centerline of the support means. The apparatus and associated method may involve providing an illuminator/flash unit, a grid, a cobalt blue filter, and an infrared cutoff filter on one side of the support means, and a video camera, and a yellow barrier filter on the other side of the support means.

If the topography of a cornea is to be obtained, fluorescein solution is applied onto the tear film of the cornea so that the grid pattern created through the grid of a Ronchi ruling becomes fluorescent when excited by light passing through the cobalt blue filter. The yellow barrier filter is employed to increase the contrast of the grid image by the video camera. When the topography of an object, other than that of a cornea is to be determined, the filters preferably are not used. The recorded image of the object is used to identify the central area of the lines of the grid pattern, to calculate the elevation of the lines of the grid pattern, and to display the elevational results in a contour plot representative of the topography of the object.

The apparatus preferably comprises a microscope with two beam splitters, a video camera and optics along a centerline in line with a support for resting and placement of an object, which in the instance of the cornea is the head of a patient. A video camera and the yellow barrier filter are located at an angle relative to and along the centerline of the apparatus, and an illuminating source, a grid, and the cobalt blue and infrared cutoff filters are located in a line relative to each other and at an angle relative to the centerline opposite to that of the video camera. An image processor is employed to determine the topography of the object through the use of software which identifies, and calculates the elevation of the grid lines, and displays the results in a contour plot representing the topography of the object.

The system, method, and apparatus may be used for obtaining the topography of an object which is transparent and nondiffusing to light, such as a cornea, or which is nontransparent and diffusing to light.

It is a broad object of the invention to provide a system, an apparatus, and a method for quickly and efficiently determining the topography of an entire surface of an object, which object is transparent and nondiffusing to light, such as a cornea, or which is nontransparent and diffusing to light.

It is a further object of the present invention to provide a system, an apparatus, and a method for quickly and efficiently determining the topography of an entire cornea of a patient, which is a member of the animal kingdom particularly a human.

It is a further object of the present invention to provide a system, a method, and an apparatus for achieving the preceding objective by obtaining information on curvature and surface detail across the full cornea surface including the central optical axis and the periphery beyond the limbus.

It is a further object of the invention to provide a system, a method, and an apparatus for effectively projecting a grid onto the object and shortening the computer time by digitizing a video image of the grid by an image processor which calculates surface detail by evaluating the distortion of the grid lines.

It is another object of the invention to provide such a system which attaches to an examination slit lamp microscope and which is compact, economical, providing valid clinical information regarding curvature and topography, particularly of a cornea, and which is easily operated by medical personnel.

It is yet another object of the invention to provide such a system which attaches to a microscope which is used in an operating room.

It is a further object of the invention to provide a system, an apparatus, and a method for quickly and efficiently determining the topography of an entire surface of an object and reproducing the results, and which system and apparatus are easy to operate, are inexpensive to buy and operate, and which system, apparatus and method are harmless to the object, especially a cornea, and are generally not unpleasant for the patient.

It is a further object of the invention to provide a system, a method and an apparatus for obtaining the topography of a cornea which enables a grid image to be reflected from the cornea.

It is a further object of the invention to provide a system, an apparatus, and a method whereby digital imaging processing techniques are used to find elevation information, from which, in turn, curvature information is extracted.

It is a further object of the invention to provide a system, an apparatus, and a method relative to the preceding objective whereby from the extracted data, an assessment of the shape of the object and the refractive power of the front surface of a cornea can be made.

A further object of the invention is to provide such a system which is compact, economical, and together with computer hardware and appropriate software is capable of making calculations in an operating room where time is of the essence.

It is therefore an object of the present invention to more effectively and efficiently obtain the topography of an object, such as a cornea, and to achieve this through a rasterstereographic technique.

It is a further object of the invention to project a grid image onto a transparent, nondiffusing object, such as a cornea rather than have the grid image reflected by the cornea, so that the projected image is not affected by surface defects and irregularities.

It is a further object of the invention to electronically acquire the image of an object, electronically digitize and analyze the imaging system, and display the data obtained from the analysis of these images in easily understood formats.

It is a further object of the invention to apply a digital image processing technique to the projected image in order to find the projected lines and to convert the lines into elevation information.

It is a further object of the invention to extract curvature information and in the instance where the cornea is being examined, diopter powers from the curvature information.

It is a still further object of the invention to use the elevation and curvature information to obtain an intuitive and quantitative assessment of the shape and refractive power of the front surface of the cornea.

A further object is to utilize computer processing techniques including a main program with a number of subroutines including an edge determining subroutine, a line segment constructing subroutine, a matrix building subroutine, an elevation computing subroutine, and a curvature computing subroutine.

It is a further object of the invention to adapt a Zeiss or a Topcon exam slit lamp microscope, which may generally have been used in stereophotographic techniques for obtaining the topography of a cornea, to a rasterstereographic method for obtaining the topography of a cornea.

A still further object of the invention is to adapt a Zeiss or a Topcon exam slit lamp microscope to a rasterstereographic method for obtaining the topography of any object.

It is a further object of the invention to provide in a rasterstereographic technique a cornea surface with a grid image projected thereon.

It is a further object to achieve the immediately preceding objective by applying a fluorescein solution onto the surface of the eye.

These and other objects of this invention will be more fully understood from the following description of the invention on reference to the illustrations appended hereto.

BRIEF DESCRIPTION OF THE DRAWINGS

FIG. 1a is an illustration of a normal spherical cornea with a placido disk used in the prior art;

FIG. 1b is an illustration of a corneal transplant patient with astigmatic central cornea using the placido disk technique of the prior art;

FIG. 2 is an illustration of an image of a vertical grid projected onto the eye obtained by the present invention;

DESCRIPTION OF A PREFERRED EMBODIMENT

Figure 3:
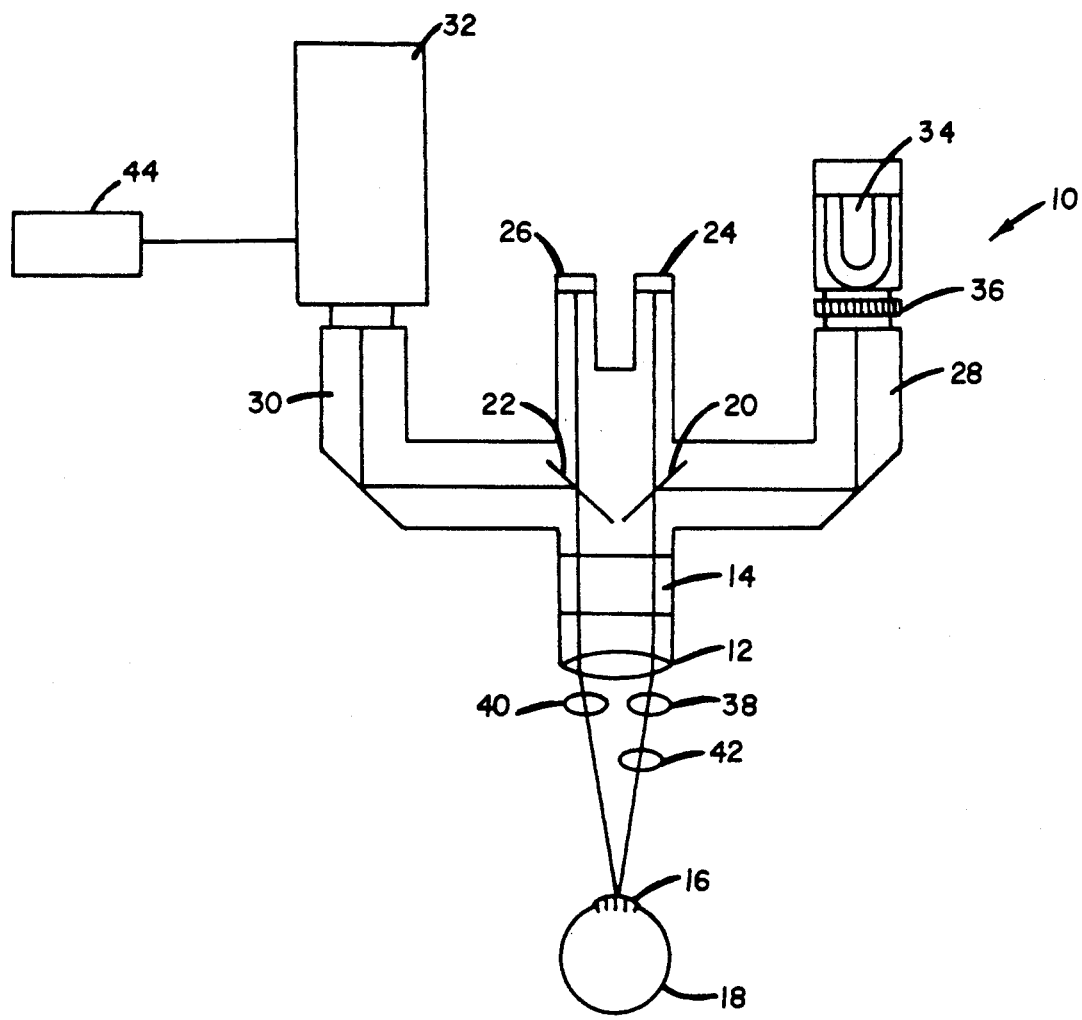
FIG. 3 is a schematic diagram of a microscope with beam splitter and projection system employed in the present invention.

The invention may be used to obtain through raster-stereographical techniques the topography of an object which is nontransparent and diffusing to light or which is transparent and nondiffusing to light, such as a cornea. The invention has particular application but is not limited as a clinical tool for the evaluation of topographic abnormalities of the corneal surface of a patient being a member of the animal kingdom, particularly a human. The invention will be described in terms of obtaining the topography of the cornea of a human, but is not limited thereto, and may be employed to determine the surface features or surface contour of an external body portion. The invention may also be used in dentistry, particularly in surgery, and also in plastic surgery practices.

Eyes that are emmetropic and eyes with keratoconus and severe astigmatism can be detected, analyzed and corrected through surgery and contact lenses. The invention can be easily used in an examination room or in an operating room.

As used herein, "limbus" is the border or edge of the cornea or clear optical zone and the sclera portion of the eye. The sclera is the white, fibrous outer envelope of tissue surrounding the cornea.

As used herein, "cornea" is the transparent anterior portion of the outer fibrous tunic of the eye, a uniformly thick, nearly circular convex structure covering the lens.

As used herein, a pixel is an individual picture element constituting a matrix used in a digital computer system for the resolution of images.

As used herein, the term "search window" applies to a size dimension which denotes how far from a reference line a search for a line segment will take place. Increasing or decreasing a "search window" means to look within a larger or smaller area about the reference line, respectively.

As used herein, the term "projection space" applies to that area on which the lines are projected, e.g., the cornea.

As used herein, the term "image space" applies to the several lines as they appear in the computer image.

As used herein, the term "fiducial mark" means a mark projected onto the measured surface.

As used herein, the term "viewing optics" or "imaging optics" are the set of optics through which the camera views the cornea.

As used herein, the term "projection optics" are the set of optics through which the lines are projected onto the cornea or onto the measured surface.

As used herein, the term "diopter" is defined as a unit of curvature and/or of power of lenses, refracting surfaces, and other optical systems.

FIG. 1a and FIG. 1b show the results of obtaining the corneal topography by the prior art practice of using the placido disk techniques. As stated hereinbefore, this technique has a placido disk consisting of a series of black and white concentric rings on a circular disk. The disk is placed in front of the eye, and the several rings are reflected by the cornea surface, and their position, size, and spacing in the reflected image are determined by the corneal shape. If the cornea is spherical, the rings appear to be round and regularly shaped as shown particularly in FIG. 1a. If the cornea is oval or astigmatic, the rings appear as being oval and the spacing between the rings varies along the different axes as shown in FIG. 1b. From these photographs it can be seen that much information is not available around the peripheral edges of the white rings in that a shadow is cast by the patient's eyelash, brow or nose.

FIGS. 2-13 illustrate the present invention. In the invention, a grid is projected onto the cornea surface and is imaged as particularly illustrated in FIG. 2. It is preferred that the present invention employ a vertical grid which projects a light and dark line pattern onto the cornea. The image of the projected light and dark line pattern on the cornea is in FIG. 2, where one such light line is indicated at 6 and one such dark line is indicated at 8. As can be seen, the projected image covers the full cornea including the central optical zone and the limbus, which is the border of the edge of the cornea between the optical zone and the sclera portion of the eye.

The projected vertical grid which is imaged in FIG. 2 may be obtained through the employment of an apparatus 10 of the invention, which is shown schematically in FIG. 3.

In FIG. 3, preferably, apparatus 10 of the present invention employs an optical system. This optical system consists of an objective lens system 12 associated with a variable magnification turret 14. In lens system 12, one lens is concave and the other lens is convex. These lenses are used to magnify the cornea. The patient preferably places his or her head in a support (not shown) of the apparatus 10 of FIG. 3 so that the cornea 16 of the eye 18 is in line with the optical system. Also in line with the cornea 16 and the objective lens system 12 are two beam splitters shown schematically by a slanted hard line at 20 and 22, and two oculars shown at 24 and 26 for viewing of the cornea 16 by the operator of apparatus 10.

Preferably, apparatus 10 of FIG. 3 is a Zeiss or Topcon stereo photo microscope with a slit lamp system, or a similar system thereto which microscope has been modified to support the components of the invention. Two cine elbows indicated at 28 and 30 are mounted to the main body portion of apparatus 10 containing the beam splitters 20 and 22. These elbows 28 and 30 are shown to the right and left respectively in FIG. 3. Preferably, elbow 30 contains the slit lamp of a typical microscope which preferably is a Zeiss Model SL-6 or a Topcon model SL-6E presently used in stereobiomicrography. Attached to elbow 30 is a video camera 32 which preferably is adapted to produce black and white images. Attached to elbow 28 is a coaxial illuminator/flash unit or projection system 34.

The Zeiss microscope, which has generally been used in a general examination of the eye, is modified by the addition of elbows 28 and 30 to support both video camera 32 and projection system 34. Mounted in front of unit 34 is a grid 36, which is a type of grating consisting only of vertical lines.

In still referring to FIG. 3, preferably grid 36 is a well-known Rhonchi ruling with a one-to-one ratio of width and space. This grid 36 is mounted along the grid projected plane of the optical system of apparatus 10 in order to focus on the cornea at a desired point. Interposed between grid 36 and cornea 16 along an optical grid projection pathway is a filter 38. This filter 38 preferably is a cobalt blue excitation filter which preferably is a Zeiss SE40 filter. Along an optical imaging pathway interposed between video camera 32 and the cornea 16 is a yellow barrier filter 40, which preferably is a Zeiss SB50 filter. An infrared cutoff filter 42, which preferably is a Kodak filter, is interposed between grid 36 and the cornea 16 along the grid projection optical pathway.

Filters 38, 40, and 42 are held in apparatus 10 through holders (not shown) which are adapted to be easily mounted on the body of apparatus 10 for keeping the filters clean, and for preventing the scatter of light illuminated by illuminator/flash unit 34. Video camera 32 is connected to an image processor unit 44 which includes a computer. The computer electronically digitizes the projected image on the cornea by the grid 36, and stores and analyzes the data obtained therefrom, more of which is discussed further herein. Processor unit 44 is preferably a PAR CTS 100 unit provided by PAR Technology Corporation of New Hartford, N.Y.

In order to obtain a rasterstereographic image of the cornea, the operator focuses the optical system of apparatus 10. Preferably, ocular 26 is brought into focus by the operator. The illumination device on the slit lamp which is normally used for projecting a slit onto the cornea during examination generally is not used in the invention. The illuminator/flash unit 34 through cine elbow 28, the beam splitters 22 and 23, and the optical system provide the illumination required for focusing the objective lens system 12 onto the cornea 16. When the objective lens system 12 is at the proper focus distance, as observed by the operator through the viewing optics, the operator of apparatus 10 triggers the illuminator/flash unit 34 which follows the same pathway through the left viewing optics of the optical system of apparatus 10. The intensity of illuminator/flash unit 34 provides sufficient intensity to produce an image of the grid 36 projected onto the surface of the cornea 16.

As the surface of cornea 16 is transparent and nondiffusing the projected grid would under ordinary circumstances not be visible on the cornea In order to provide a fluorescing surface on the eye to allow the projected grid to be visible, the invention employs a sodium fluorescein solution which is applied to the external corneal surface to stain the tear film of the eye. A sodium fluorescein solution which is commercially available and may be employed is known as Fluress, provided by Barnes Hind which contains 0.25 percent sodium fluorescein. The light from the flash of unit 34 passes through the cobalt blue filter 38 and the infrared cutoff filter 42.

As discussed hereinbefore, the cobalt blue filter 38 causes the fluorescein solution in the tear film on the surface of the eye to fluoresce in an alternating light and dark pattern which is produced by grid 36, and the infrared cutoff filter 42 shields the patient from the infrared transmissions of the flash tube unit 34, which unit 34 may be driven by approximately 400 volts.

This alternating light and dark line pattern is viewed by the video camera 32 through the yellow barrier filter 40 which as discussed hereinbefore, is used to increase the contrast of this alternating grid pattern. An example of this pattern is shown in FIG. 2. This image is automatically and electronically digitized and the data is stored and analyzed by image processor unit 44, through a procedure which is explained further with reference to FIGS. 4–13.

The apparatus 10 of the invention can be used in either an operating room or in an examination room. In the case where it is used in an operating room, preferably the objective lens 12 will have a focal length of approximately 175 millimeters. In referring again to FIG. 3 the angle formed by the plane along the centerline of the apparatus 10 and the projected optical pathway in which grid 36 and projection system 34 is located preferably will be about 6 degrees. This same angle will exist on the left side of apparatus 10 between the centerline and the imaging optical pathway where video camera 32 is located. Preferably the projection system 34 is spaced 100 millimeters away from cornea 16.

If the instrument 10 is to be used in an examination room, then preferably objective lens 12 will have a focal length of 100 millimeters. This shorter focal length objective will cause the angle between the centerline of apparatus 10 and the projected optical pathway and the angle between the centerline of apparatus 10 and the imaged optical pathway to become wider, i.e., the angle will become greater than the 6 degree angle existing when a 175 millimeter objective lens 12 is used.

If apparatus 10 of FIG. 3 is to be used to determine the topography of a solid object or a nontransparent object which is diffusing to light, then filters 38, 40 and 42 should not be used. Also, it is not necessary to apply the fluorescein solution to the object.

A feature of the present invention involves applying digital image processing techniques to the projected image of FIG. 2 to find the projected lines and to convert these lines into elevational information. Curvature information for the cornea is then extracted from the elevational information.

By using the elevation and curvature information the operator can obtain an intuitive and quantitative assessment of the shape and refractive power of the front surface of the cornea, or of the object under examination.

1. Computer Analysis

The computer analysis is discussed with reference to a cornea, however, here again, the procedure and results can quite easily be applied to any object under examination by apparatus 10, such as external body portions of both humans and other animals.

With regard to FIG. 2, the position and spacing of the vertical lines on cornea 16 provide the necessary information for determining the corneal topography. The computer of image processing unit 44 through an appropriate program is used to calculate the corneal surface elevation trigonometrically by comparing the horizontal displacement of the grid lines projected onto the cornea to the position of the vertical grid lines when projected onto a two-dimensional flat plane.

From these data, a two-dimensional matrix of elevation points is created. The number of data points in a horizontal direction is equal to the number of actual projected grid lines. The number of data points in a vertical direction for each grid line is limited only by the resolution of the system of video camera 32.

In order to limit the computer processing time, a vertical scaling proportional to a horizontal scaling is used. Preferably, surface elevations are calculated on a full cornea and the sclera. As discussed hereinbefore, the sclera is the white, fibrous outer envelope of tissue surrounding the cornea. In FIG. 2, it is apparent that the cornea covering the pupil and the iris is completely represented with the sclera surrounding the cornea around its periphery which is substantially darkened in FIG. 2. The grid lines of FIG. 2 vary in shape and intensity.

In the example of FIG. 2, in accordance with the invention the cornea was made opaque by topically applying the fluorescein solution onto the outer surface of the cornea, and the grid 36, through the cobalt blue filter 38, was projected onto the eye 18.

When performing elevational calculations on the full cornea and sclera, the spacing between horizontal points for the two-dimensional matrix is approximately 0.4 millimeters. If desired, a higher magnification can be used, reducing this distance to 0.1 millimeters. The resultant matrix size then is approximately 45 horizontal data points by 60 vertical data points for a total greater than 2500 elevation points across the surface of the cornea.

Figure 4:
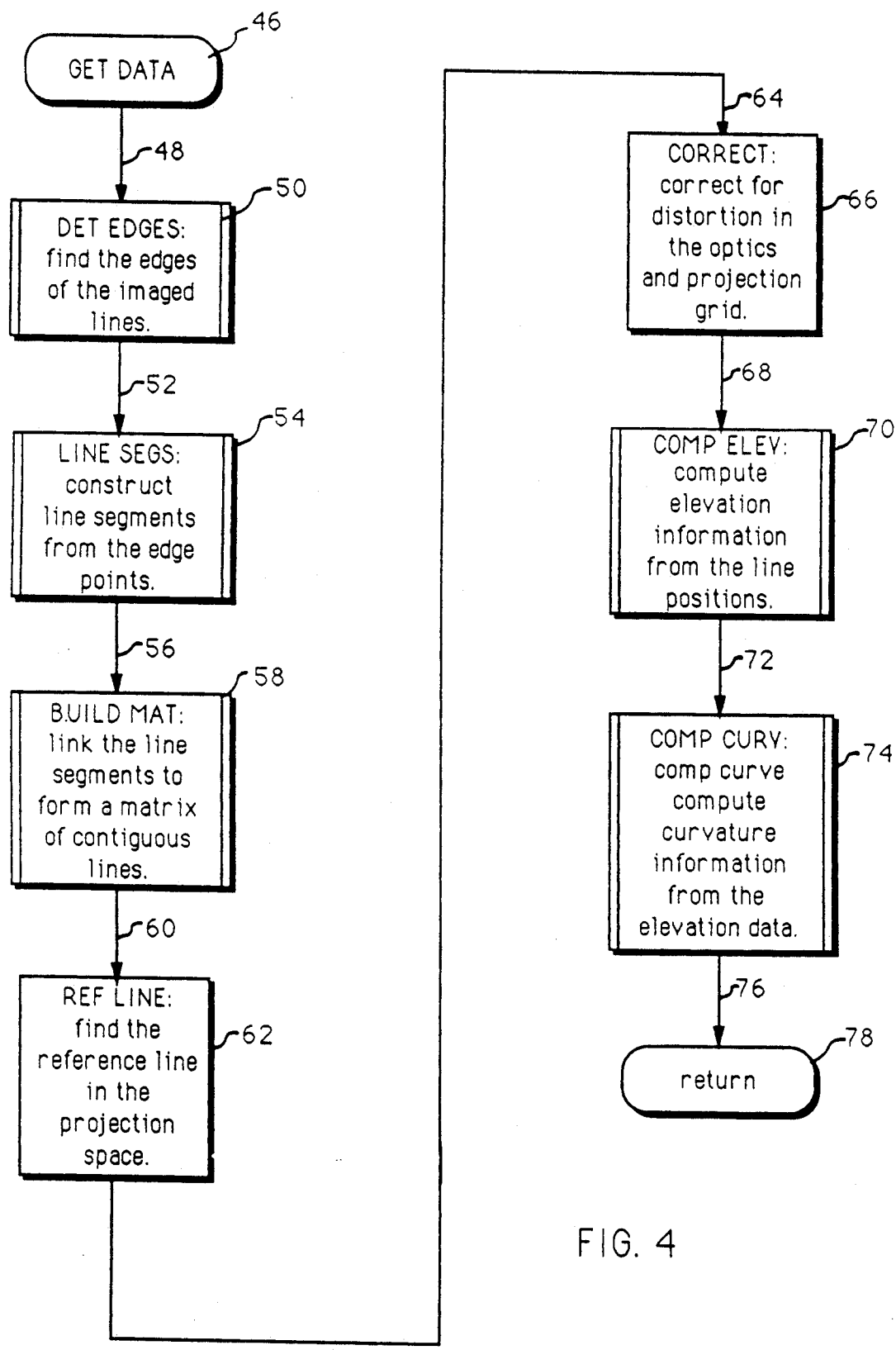
FIG. 4 is a logic flow diagram of the main program for digitizing the image on the cornea of FIG. 2 by a computer.

The software for the image processing unit 44 is illustrated in terms of flow diagrams in FIGS. 4-8. The main software program for determining the topography of the surface of a cornea is illustrated in FIG. 4 and is written in terms of subroutines, the flow diagrams for which are shown in FIGS. 5-8. These computer programs have been developed (a) to identify the grid lines, (b) to calculate the elevation points from which curvature information is derived which has been discussed to some length hereinbefore, and (c) to display the results.

Referring more specifically to FIG. 4, the main software program of processing unit 44 of FIG. 3 sets forth several directives for performing steps (a), (b), and (c) in the preceding paragraph. The first step is to obtain the data of, for instance, the imaged grid lines on the cornea of FIG. 2. This step of obtaining this data is indicated at 46. The imaged grid lines are those that appear in the computer image.

Once the data is obtained, the processing unit 44, as indicated at 48, employs the first subroutine indicated at 50 and identified as "DET EDGES". As is apparent, this subroutine finds the edges of the imaged grid lines on the cornea. From this the main program moves down as indicated at 52 to the next subroutine indicated at 54, and entitled "LINE SEGS". This subroutine is designed to construct a line segment from the edge points found in the subroutine "DET EDGES".

Once all the line segments are constructed the main program moves down as indicated at 56 to the subroutine entitled "BUILD MAT" indicated at 58. This subroutine is designed to link the line segments together to form a matrix of contiguous lines. After the elevation of the imaged grid lines are computed, two additional steps indicated by numbers 60, 62, 64, and 66 are performed by processing unit 44. The first step indicated at 62 is referred to as "REF LINE". This step finds the reference line in the projection space. A correction for the distortion in the optics and in the projection grid lines is found by the step indicated at 66 and is referred to as "CORRECT".

These two steps lead as indicated at 68 to the next subroutine entitled "COMP ELEV". This subroutine is designed to compute the elevation of the imaged grid lines from the line positions found by the previous subroutine. This subroutine "COMP ELEV" is followed as indicated at 72 by the subroutine indicated at 74 entitled "COMP CUR".

This "COMP CUR" subroutine is designed to compute the curvature information of the cornea from the elevation data obtained in the subroutine "COMP ELEV".

The subroutine for computing the curvature is not disclosed herein but is indicated as being a preferred step in the invention. The method preferably used in the invention for calculating the radius of curvature is the simplex computer algorithm to best fit an arc to the elevation points. This simplex algorithm is well-known in the computer industry where software is readily available.

Once the curvature is determined, the main program of FIG. 4 is exited, and the processing unit 44 through a display device (not shown) visualizes the results of the algorithm of FIG. 4, as shown for instance in FIGS. 10, 11, 12, and 13, more of which is to be discussed hereinafter along with more details of the several subroutines of FIGS. 5, 6, 7, and 8.

(a) Identifying the Grid Lines

A further description of the several subroutines of the algorithm of FIG. 4 will now be given.

Referring again to FIG. 5, the first subroutine "DET EDGES" is called up by the main program to determine the edges of the imaged lines. At this time the lines of the vertical grid 36 projected onto the cornea are visible in the digitized image.

Figure 5:
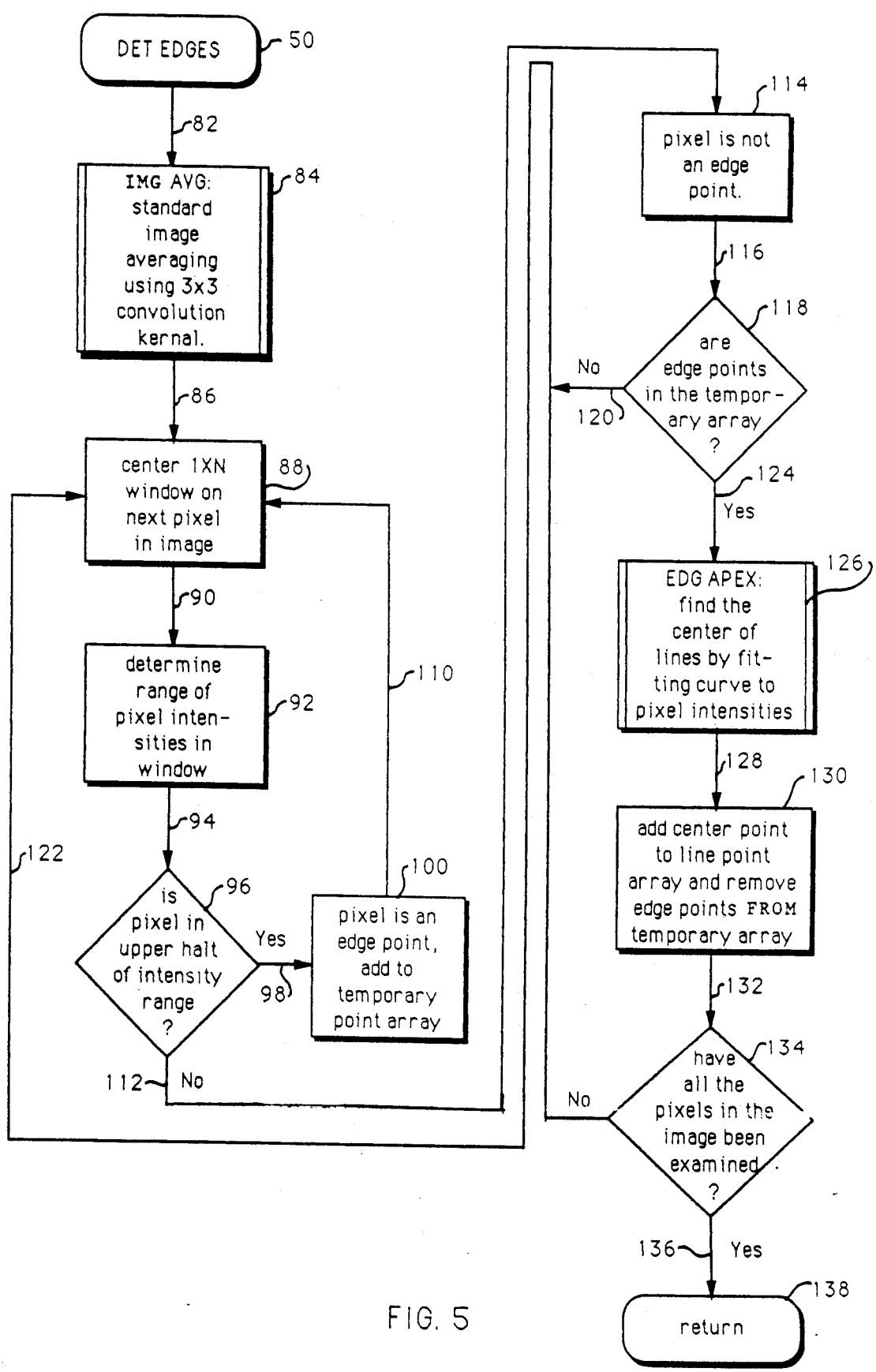
FIGS. 5, 6, 7, and 8 are logic flow diagrams of subroutines utilized in the main program of FIG. 4 including respectively a determination of the edges subroutine; a construction of the line segments subroutine a forming of a matrix subroutine; and a computation of the elevation in formation subroutine.

This subroutine of FIG. 5 is designed to attempt to find the edges of the projected lines of every third row of the image. This algorithm of FIG. 5 uses the wavelike distribution of pixel intensities related to the light to dark transition of the lines to find the near exact center of each line.

The subroutine of FIG. 5 illustrates the several steps involved in accomplishing this. The first step as indicated at 82 and 84 is to use a $3 \times 3$ convolution kernel to perform a standard image averaging on the whole image. The second step as indicated at 86 and 88 is to center a $1 \times N$ window on a pixel in the image. The third step as indicated at 90 and 92 is to determine the range of the pixel intensities in the window. This is accomplished by looking at the numeric pixel intensities of the pixels in the window for the lowest and the highest values. These values mark the range. As indicated at 94 and 96 the next step is to determine if the pixel is in the upper half of the intensity range.

If the answer is "yes" as indicated at 98 and 100 then the pixel is considered to be an edge point. This edge point is added to a temporary point array. As indicated at 110, from the step in block 100, the subroutine goes back to block 88 where these steps are repeated for the next pixel in the image. If the pixel under study is not in the upper half of the intensity range, then as indicated at 112 and 114 the pixel is not considered to be an edge point.

The next step is to ask whether there are any edge points in the temporary array. This is indicated at 116 and 118. If the answer is "no," then as indicated at 120 and 122 the subroutine returns to block 88 to examine the next pixel in the image. If the answer is "yes," then as indicated at 124 and 126 the program proceeds to the step entitled "EDG APEX".

This algorithm in FIG. 5 finds the center of the line formed by the points in the temporary array by fitting a curve to the pixel intensities of the edge points. As numbers 128 and 130 indicate the center point is added to the line point array, and the edge points are removed from the temporary array. The final step is indicated at 132 and 134 where it is determined as to whether all the pixels in the image have been examined.

If the answer is "no," then the program returns to the appropriate location of block 88 whereby the next pixel in the image is examined. If "yes," the subroutine program returns to block 54 of the main program of FIG. 4 as indicated at 136 and 138.

Figure 6:
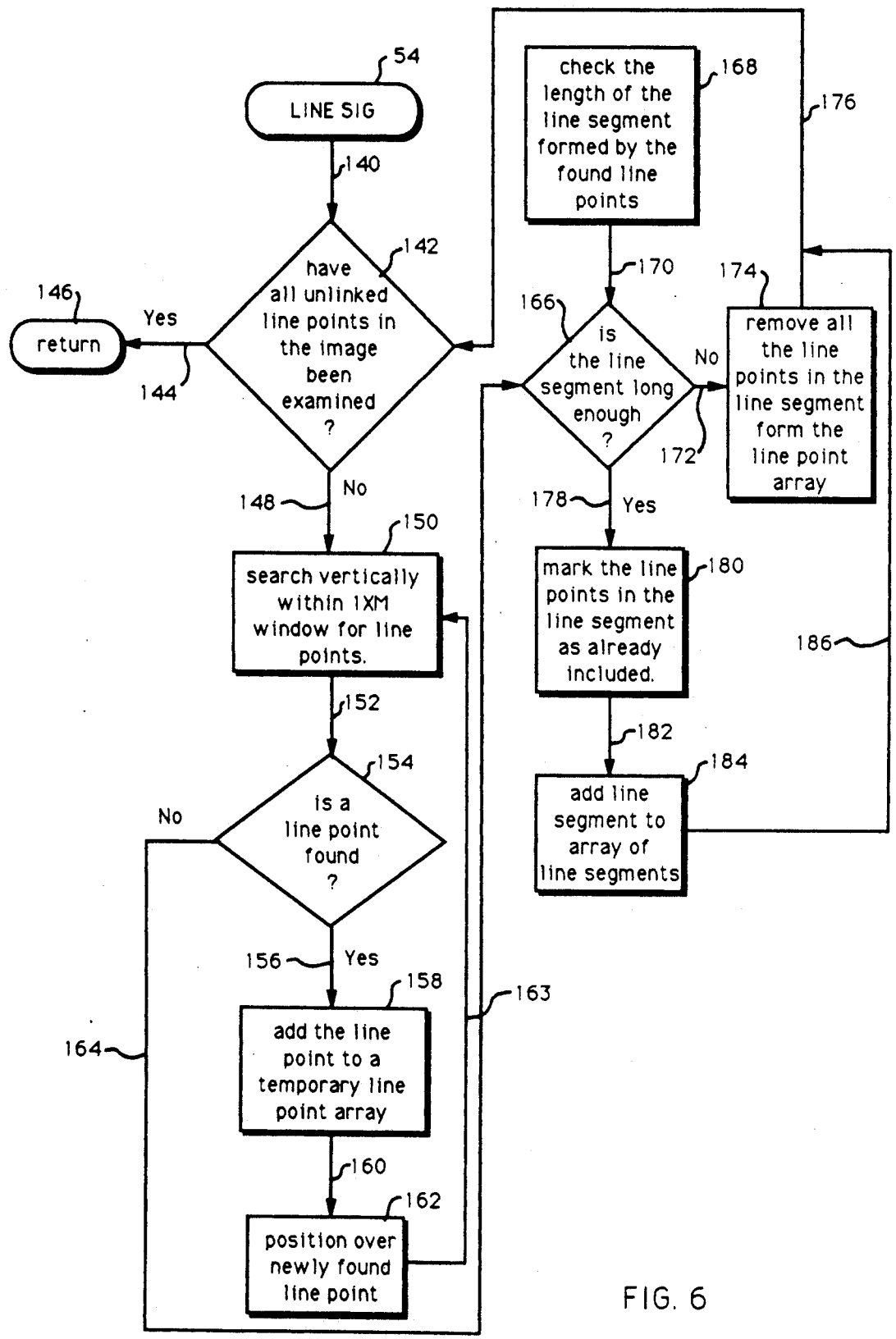

The flow diagram of the subroutine of FIG. 6 is identified as "LINE SEG", and is used to construct line segments from the line points. This portion of the main program is activated when all the line points of the lines of every third row of the image have been found by the subroutine of FIG. 5.

This algorithm of FIG. 6 attempts to link the several line points to form a series of continuous line segments. In order to account for possible noise from not being included, restrictions are applied when linking the line points.

A root line point is found. When searching for other line points which are linked to a root line point, a search window is specified in which the search is made. This limits the possibility of incorrect line points being linked to form a line segment. Once the line segments are found, a length restriction is applied to discard those line segments which may have been inadvertently created. Referring specifically to FIG. 6, the flow diagram of this subroutine illustrates the several steps involved in forming the line segment forming operation.

The first step as indicated at 140 and 142 is to ask whether all the unlinked line points in the image have been examined as specifically shown in block 142. If "yes," then the subroutine returns to the main program of FIG. 4 as indicated by numbers 144 and 146. If "no," a further search is made vertically within a 1×M window for neighboring line points as indicated at 148 and 150. The question "Is a line point found?" is asked as indicated at 152 and 154. If a line point is found, the line point is added to a temporary line point array as indicated at 156 and 158.

The next step from the step at 158 is to position the 1×M search window over the newly found line point and to find other line points linked to the newly found or root line point by a continuous search as indicated at 160 and 162. From 162, the subroutine by line 163 returns to block 150. If no line point is found by the step at 154 then as indicated at 164 the question is asked at 166 as to whether the line segment is long enough.

As indicated at 168 and 170 the algorithm of FIG. 6 is designed to check the length of the line segment formed by the found line points followed by asking the question indicated at 166. If "no," then all the line points in the line segment are removed from the line point array as indicated at 172 and 174, and the subroutine returns to 142 to the beginning of this loop as indicated at 176. If "yes," then as indicated at 178 and 180 the line points in the line segment are marked as being included.

As indicated at 182 and 184 of FIG. 6, one of the final steps is to add the line segment to the array of line segments. From this step, the algorithm returns as indicated at 186 to the beginning of the subroutine at 142. If certain conditions are met, this algorithm is completed and the operation is returned to the main program of FIG. 4.

Figure 7:
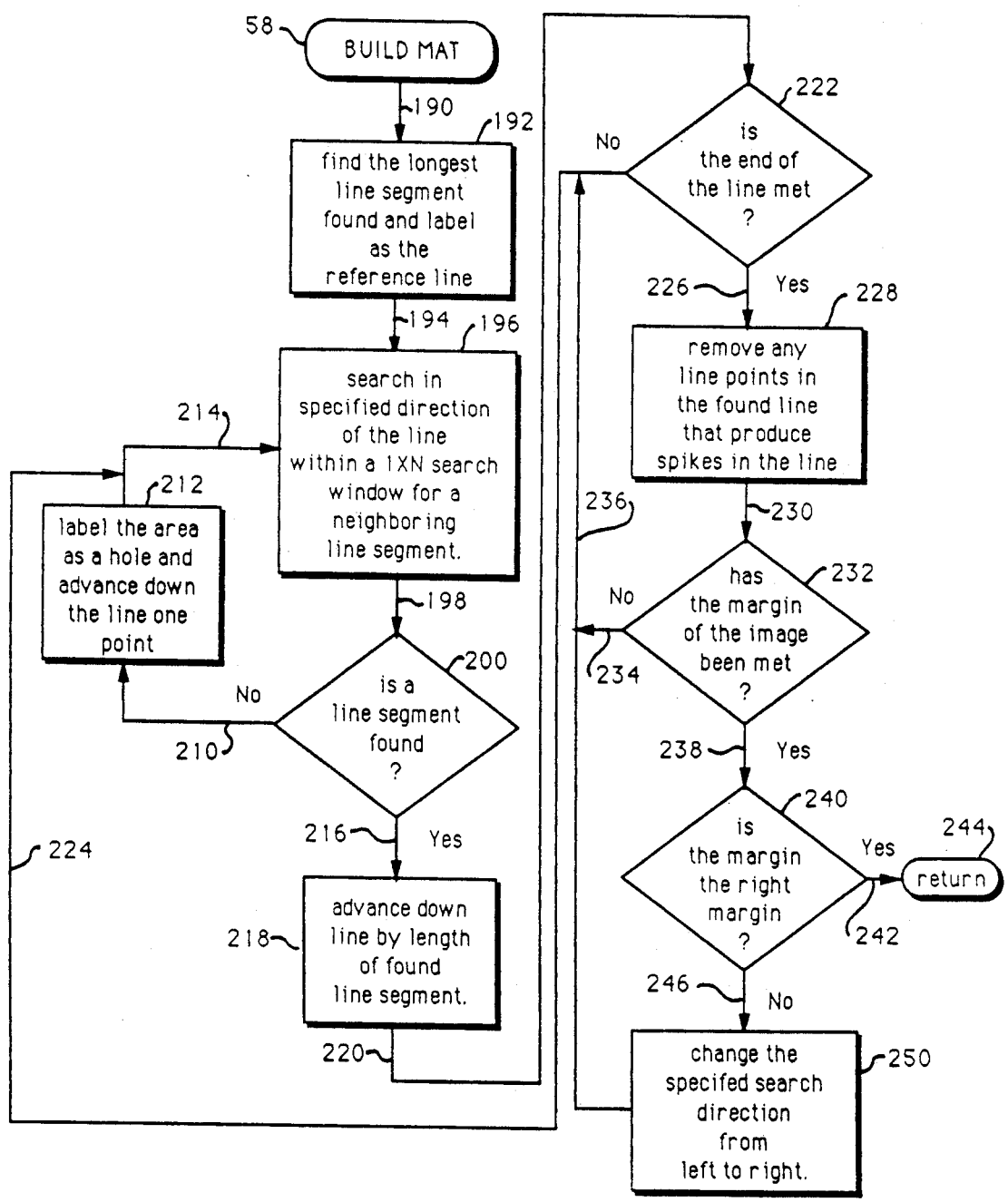

Once continuous line segments are formed by the subroutine of FIG. 6, the next step is to link the line segments to form a matrix of contiguous lines. The subroutine of FIG. 7 illustrates the several steps for performing this operation. These contiguous lines are referenced relative to each other in order to determine their position on the cornea.

This process involves first finding the longest line determined in the "Line Seg" subroutine of FIG. 6. This line is used as a reference line. The subroutine of FIG. 7 entitled "Build Mat" then looks horizontally to find the next vertical line segment. The search is for each line point in the reference line segment constrained within a search window. If a line segment is not found within the allowed range then there is no data next to the reference line at this line point position. The search continues for every line point in the reference line. Once all the line points in the reference line have been searched, a second test for line point validity is applied. The average spacing between the reference line and the newly found line is computed. This is done by finding the difference between the average horizontal positions of all the line points in the reference line and the average horizontal position of a line point in the new line. Any line points in the newly found line which are farther than 1.5 times the average spacing commonly referenced to as "spikes" are excluded from the new line.

This procedure for the reference line is then repeated for the newly found line which then becomes the reference line. The search window is also changed from the previous dimension to 1.5 times the average spacing which has just been computed.

The search window is a size dimension which denotes how far from the reference line a search for a line segment will take place. Increasing or decreasing the search window means to look within a larger or smaller area about the reference line respectively.

The final output of the subroutine of FIG. 7 is a two-dimensional array of image positions denoting the points of the located lines.

The subroutine of FIG. 7 continues to reference line segments starting at the first reference line and proceeding to the left side of the image until the left side of the image is reached. The subroutine then returns to the original reference line and repeats the same process but this time moving to the right side of the image. When the right side of the image is reached, all the line segments have either been linked to form continuous lines or have been discarded.

The several steps involved for the final output are shown in the algorithm of FIG. 7. The first step is to find the longest line segment and to label it as the reference line as indicated at 190 and 192. The next step is to make a search in a specified direction within a 1×N dimension search window for a neighboring line segment as indicated at 194 and 196. From this, the next step as indicated at 198 and 200 is to ask whether a line segment is found.

If "no," then as indicated at 210 and 212 in FIG. 7 the area is regarded as an empty space, and the search is advanced to the next point in the reference line from 212. From 212, the algorithm returns to the step of 196 as indicated at 214. If "yes," then as indicated at 216 and 218 the search is advanced down the line equivalent to the length of the found line segment.

The next step is to then ask whether the end of the reference line is met as indicated at 220 and 222. If "no," the subroutine returns as indicated by 224 to the beginning of the main loop of this subroutine to continue the search by the step at 196. If "yes," the next step is to remove any line points in the found line that produce "spikes" or deviations from the found line as indicated at 226 and 228.

The next question as indicated at 230 and 232 in FIG. 7 is to ask whether the margin of the image has been met. If "no," then as indicated at 234 the subroutine by way of line 236 returns to the beginning of the main loop to continue the search by the step at 196. If "yes," the next step is to ask if the margin is the appropriate one as indicated at 238 and 240. If the answer is "yes," the subroutine as indicated at 242 and 244 returns to the main program of FIG. 4. If the answer is "no," the directive is given to change the specified search direction from left to right as indicated at 246 and 250, and the subroutine is returned as indicated by line 236 to the beginning of the main loop to continue the search by the step at 196.

Figure 8:
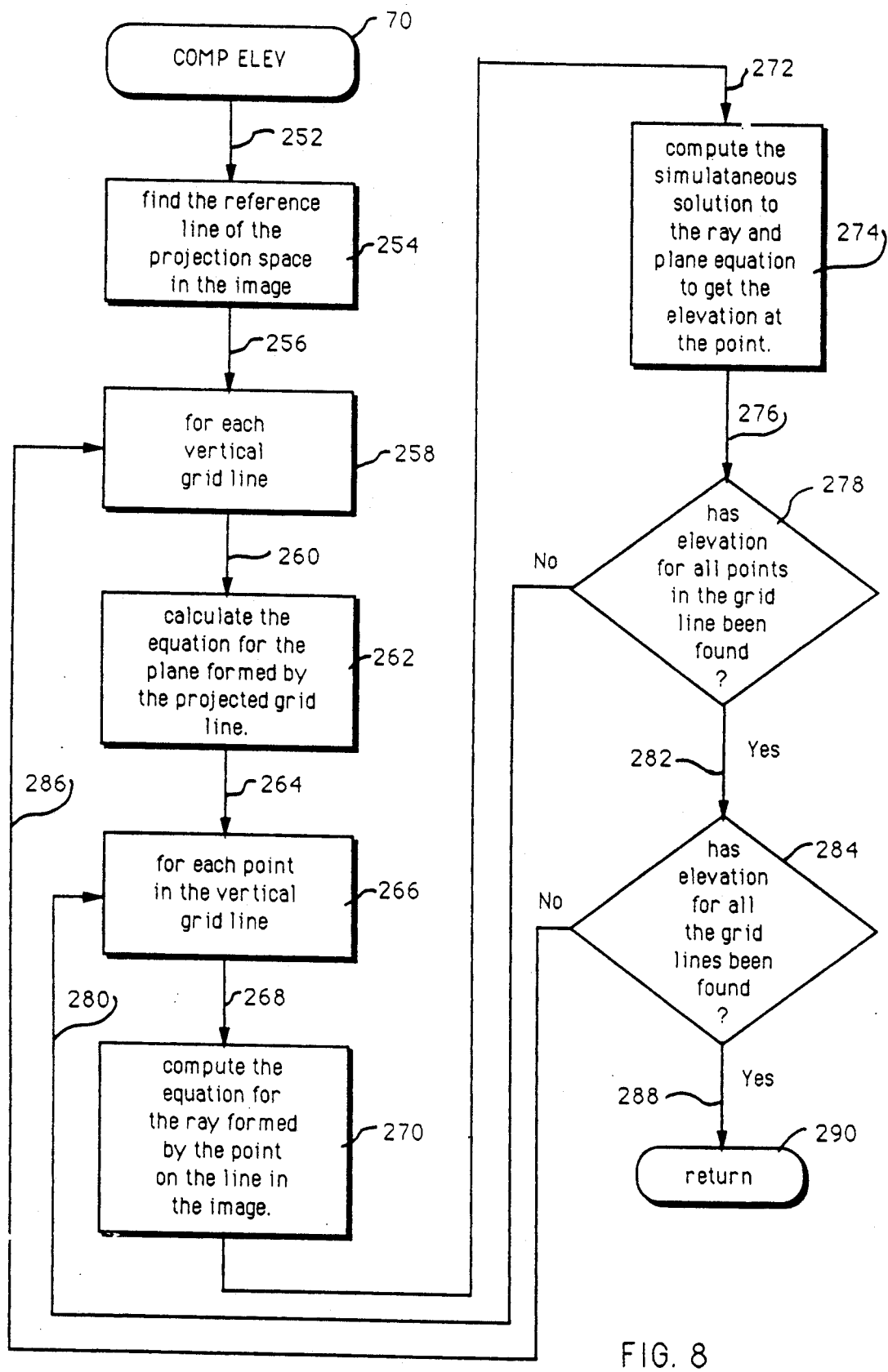

Steps 62 and 66 of the main program of FIG. 4 indicate the two additional processes which are preferably completed before the subroutine of FIG. 8 is employed.

As Step 62 indicates, the next process is to find the reference line found in the "BUILD MAT" subroutine in the projection space. To clarify this, once all the lines have been located in the image space which as mentioned hereinbefore are those lines as they appear in the computer, their location within the projection space is determined. The projection space as defined is the cornea onto where the lines are projected.

This preceding step is done in order to calculate the correct elevation and to perform correction for distortion. The system locates a fiducial mark which is regarded as a standard of reference on one of the lines. The position of this line in the projection space is known and from this known position all the remaining lines are referenced to the projection space.

A fiducial mark is formed by introducing a 'break' in one of the lines in the grid used to form the projected lines. If the lines are focused properly onto the cornea, the break in the line will appear at a specific set location in the image The "BUILD MAT" subroutine of FIG. 7 will check this known location against the location of holes that have been found If no hole has been found at this location the lines were not focused properly. The operator of apparatus 10 is informed of this and he or she must take another picture to process.

Since this fiducial mark position is known at optimum focus on the cornea, it is also known at optimum focus on a flat plane. Since all lines are referenced to each other, and, in turn the fiducial mark, the actual displacement of each line from its actual position on a flat plane can be determined.

The step in No. 66 provides for a correction for any distortion in the optic system and in the projected grid 36 of apparatus 10. Since the optics and the grid 36 are not ideal, there will be inevitably some distortion and imperfections in the system. In order to assure accuracy, this must be corrected.

These corrections are obtained by analyzing a known flat surface during a calibration procedure. The deviations from the flat surface are recorded and later applied to the lines projected onto the corneal surface. In the calibration procedure the grid spacing on the flat surface or plane is a known constant; any elevation or depression from this plane deviates the grid line according to the following Equation No. 1:

$$Deviation\ of\ Grid = (Lines\ shifted \times SP) - HD,$$

where the lines shifted is the number of grid lines which are either positive or negative from the reference line to the line to be measured, SP is the grid spacing constant as projected onto the flat plane, and HD is the horizontal distance measured along a horizontal of the flat plane from the reference point to the point on the line to be measured.

(b) Calculating the Elevation Points and Computing Curvature Information

Once the lines and their locations within the projection space are known, the elevation information is determined according to the subroutine of FIG. 8 having the heading "COMP ELEV". The operation of this subroutine involves knowing the geometry of the optical system and the video camera 32 used in the imaging procedure performed by apparatus 10 of the invention.

One of the important steps for computing the elevation of the points is to determine the equation of the plane formed by the grid line.

The equation of the plane formed by the grid line is determined by a calibration step. This step involves projecting the lines onto a flat surface. The lines are then detected and referenced as stated hereinbefore. For each vertical line two points on the line are used. One point is from the upper half of the line and the other point is from the lower half of the line. By knowing the focal length of the optics (focal length of a standard C-mount adaptor is 35 millimeters), the distance between the stereo optical pathways and the focal length of the objective lens 12 of the optical system to a 'ray' for each point can be calculated using standard vector mathematics and standard 'pin-hole camera' geometric principles.

Once the two rays have been found, the equation for the plane can be found by computing the vector cross product of the two vectors. This is performed for each vertical line and is stored in a file in the computer. This file is retrieved whenever a measurement is made.

The next step is to determine the equation of the ray formed by each point in the imaged lines. This is performed for each line point in each line found projected onto the corneal surface. This produces a ray for each line point in the line. The ray representing the point in the line and the plane of the line are solved simultaneously to determine the point of intersection. This is done using standard ray/plane intersection vector mathematics, the methods of which are outlined in standard analytical geometry textbooks.

Programs for determining the two equations and for simultaneously solving the two equations are readily available in the computer industry. The final result or output is a two dimensional array of elevation information for the front surface of the cornea which, in fact, is the topography of the front surface of the cornea.

The subroutine of FIG. 8 shows the several steps involved in computing the elevational information, as described hereinabove. The first step as indicated at 252 and 254 is to find the reference line of the projection space in the image. For each vertical grid line the equation for the plane formed by the projected grid line is looked up as indicated at 256, 258, 260 and 262. Then, as indicated at 264, 266, 268, and 270 for each point in the vertical grid line, the equation for the ray formed by the point on the line in the image is computed.

The next step as indicated at 272 and 274 is to compute the simultaneous solution of both the ray and the plane equations in order to obtain the elevation at that point. The next step is to inquire as to whether the elevations for all the points in the grid line have been found as indicated at 276 and 278. If "no," the subroutine as indicated at 280 returns to 266 which forms an inner loop which produces this result for each point in the vertical grid line. If the answer is "yes," the next inquiry as indicated at 282 and 284 is whether the elevation for all the grid lines has been found. If "no," the subroutine as indicated at 286 returns to 258 forming the main outer loop for this subroutine. If "yes," the subroutine returns to the main program of FIG. 4 as indicated at 288 and 290.

Figure 9:
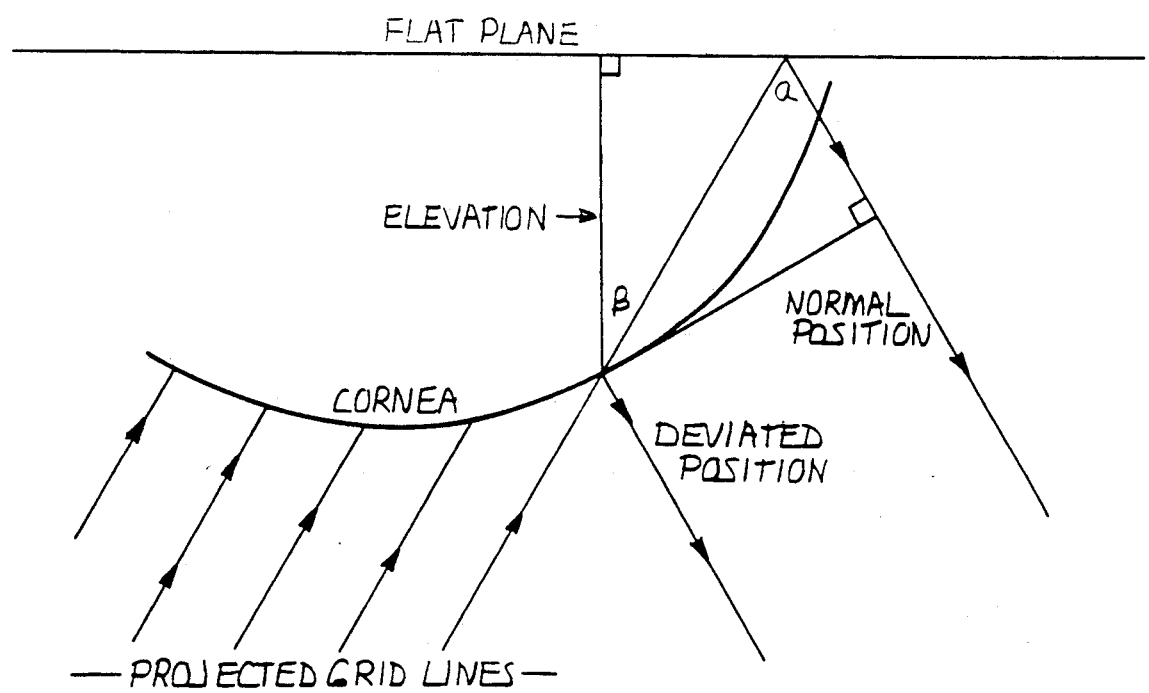
FIG. 9 is a schematic diagram showing grid lines displaced on the cornea from an assumed normal position and a trigonometric solution for elevation employed by the present invention.

Referring now to FIG. 9, there is illustrated the projected grid lines onto the cornea, and a normal positioning and a deviated positioning for the lines.

The greater the elevation of the cornea, i.e., the closer it comes to the projection and imaging lens 12 in FIG. 3, the greater a grid line deviates toward the projection lens side, or to the left in referring to FIG. 9. The matrix point elevations that are calculated from the grid line in the immediately preceding sentence are also moved proportionately to the left.

This establishes the relationship between the topography of the cornea and its effect on the movement of the projected lines. If a line is projected onto a surface and the surface is moved away from the lens 12 in FIG. 3, the line would appear to move to the right in the image. A series of vertical lines would appear close together when the surface upon which they are projected is moved close to lens 12, and become farther apart as the surface is moved away from lens 12.

The relationship between line movement and elevation change is denoted by Equation No. 2 which is derived from FIG. 9:

$z = cos\beta \times h / sin\alpha$ where:
$\alpha$ = angle between the imaging pathway and the projection pathway,
$\beta$ = half of angle $\alpha$,
h = the change in the line position on the cornea, and
z = the elevation change.

As stated hereinbefore, a two-dimensional array of elevation information is obtained by the flow diagram of the subroutine of FIG. 8. This matrix can then be stored for future use or processed for further image analysis, including computing the curvature information of the cornea.

The subroutine as indicated at 72 and 74 of FIG. 4 entitled "COMP CUR" performs the function for obtaining the curvature information. In this subroutine, the elevation information is converted into curvature information by any of the well-known methods for fitting curves to data. Preferably in the invention, the fitting of a curve to data is done by a simplex algorithm method, which is set forth in a standard math textbook. The simplex algorithm may preferably be a computer program easily available in the computer industry.

Reference for fitting curves to data by the simplex algorithm is made to an article entitled "Fitting Curves to Data, The Simplex Algorithm Is the Answer," by M. S. Caceci and Wm. P. Cacheris, Byte Magazine, May, 1984. The computer of processing unit 44 displays a cross sectional view of the cornea along any axis by plotting the elevation points of the matrix along any particular line. The radius of curvature is calculated using the same method.

Curvatures can be determined for any axis either for the average across the full cornea or for a small portion of it. The final step is to write out the values and to return this subroutine to the main program of FIG. 4 in order to produce the desired displays similar to that shown in FIGS. 10-13.

(c) Displaying the Results

Figure 10:
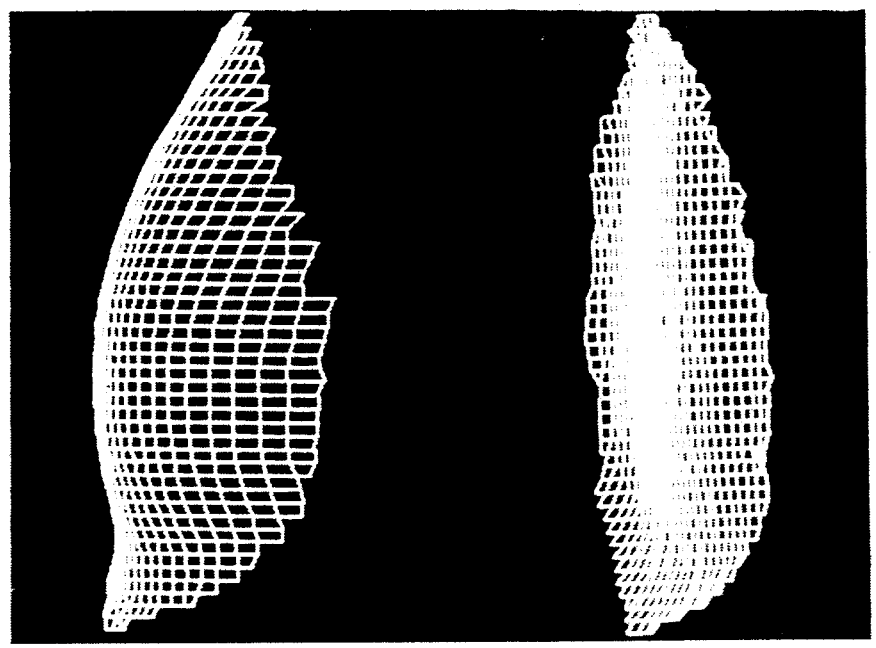
FIG. 10 is an illustration showing on the left hand side an orthogonal view of a normal cornea, and on the right hand side the same cornea with the common curve removed which are derived by the display methods used in the present invention.

Using the matrix file formed in the subroutine of FIG. 8, and by calculating the curvature, an image of the cornea can be represented in several forms, some of which are demonstrated in FIGS. 10, 11, 12, and 13. Standard graphics processing techniques which are known in the computer industry can be used to rotate the cornea around the X or the Y axis. The left portion of FIG. 10 shows an orthogonal view of a normal cornea rotated 80 degrees to the right to view the shape of the cornea across the bridge of the nose. The right portion of FIG. 10 shows the same cornea from the same angle, but the common curve of the cornea has been subtracted out to accentuate distortions from a spherical shape.

Figure 11:
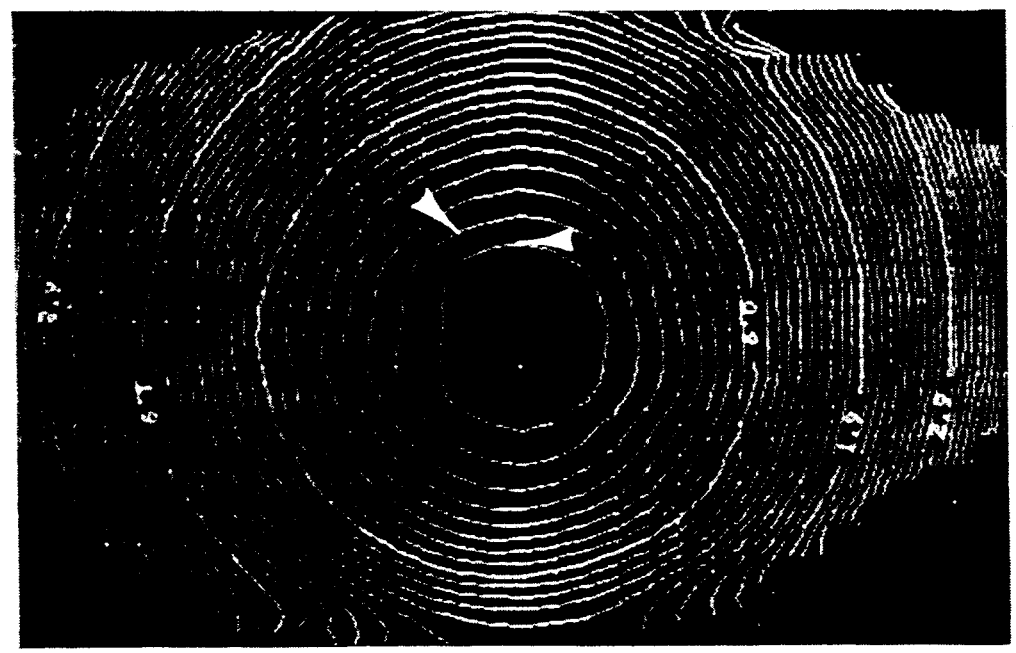
FIGS. 11, 12, and 13 are illustrations of contour plots of the cornea derived by the display methods employed in the present invention.
Figure 12:
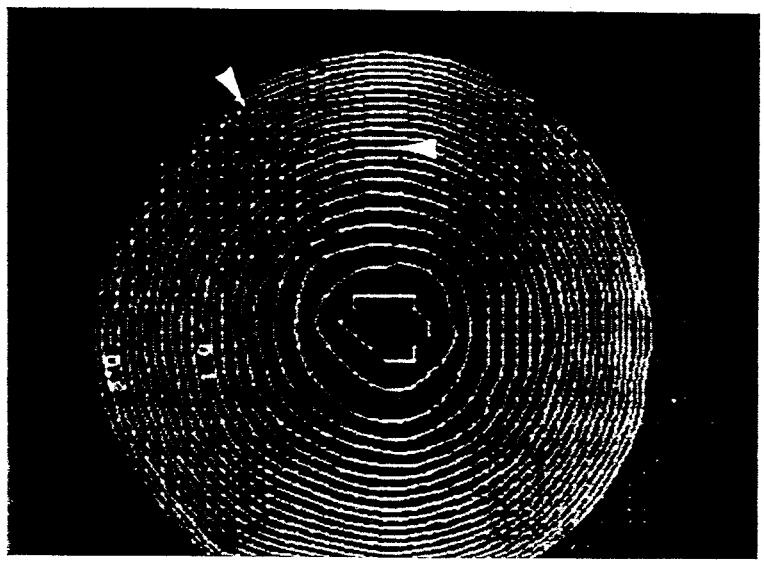
Figure 13:
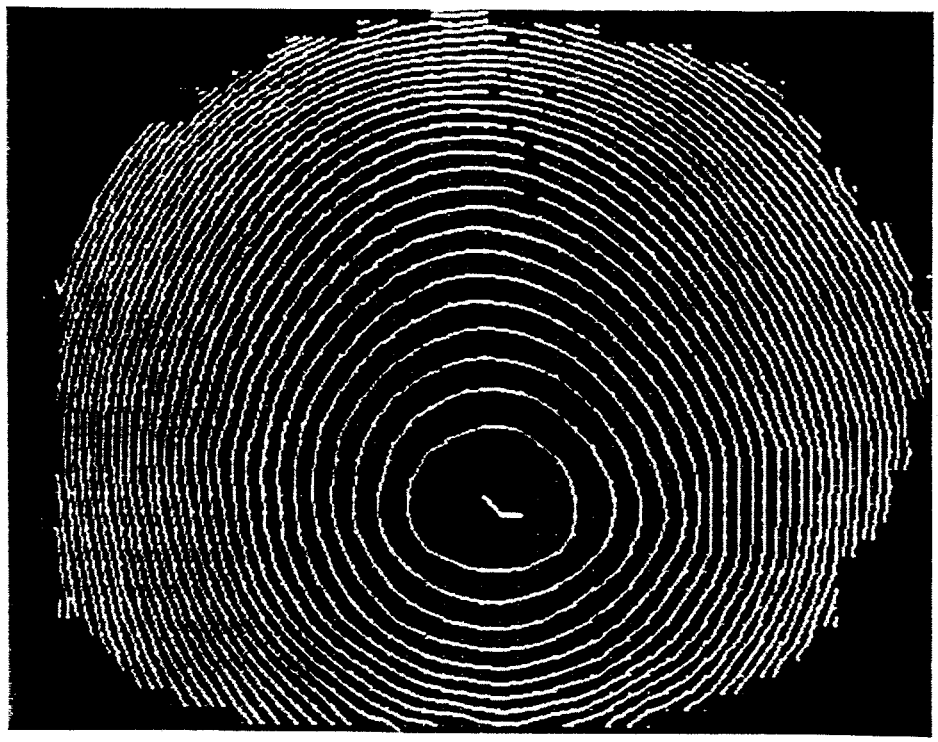

Contour plots of the cornea are also shown in FIGS. 11, 12, and 13. In FIG. 11, each line on the plot represents an area of equal height. In FIG. 11, each line represents an elevation change of 0.1 millimeters. The image of FIG. 11 is magnified 2.5 times to obtain the data for FIG. 12. Each contour line in FIG. 12 represents 0.0125 millimeters in elevation. In view of the higher magnification rate of FIG. 12, only the central 3 millimeters of the cornea is represented FIGS. 11 and 12 illustrate that the topography of a portion of the cornea represented therein is substantially curved.

FIG. 13 illustrates a full cornea of a patient with astigmatism, where the circles of the contour plot illustrate a substantially flatter topography for the cornea in the horizontal plane.

The system of the present invention comprising the apparatus 10 of FIG. 3 and the main program of FIG. 4 was calibrated using four steel balls of varying diameters as a standard for measuring curvature. The balls were sprayed with paint to provide a non-reflective surface and then measured with a micrometer.

Using the projected grid 36 each ball was photographed a total of four times. The images were processed to find a radius of curvature. The average error of the sixteen measurements was 0.060 millimeters with a range of +0.11 to −0.16 millimeters. For the larger diameter balls, the system of the present invention tended to overestimate the true curvature, while for the smallest diameter ball, the system tended to underestimate the true curvature of the ball. For each of the four balls the measurements were approximately 0.10 millimeters or less. This calibration technique for obtaining a measurement for curvature is familiar to those skilled in the art.

The accuracy of the method of the invention is dependent on several variables. These variables are: the resolution of video camera 32; the magnification of variable magnification turret 14; the angle α, between the projected image and the viewing optics; and the number of projected lines of grid 36. As the magnification of the corneal image increases, or the resolution of the video camera 32 increases, the change in depth represented by each pixel is reduced, thereby increasing the accuracy of the measured displacement of the lines of grid 36.

The following paragraphs have reference to Equation No. 2 where $z = (\cos \beta \times h)/\sin \alpha$ of FIG. 9.

If the magnification were increased, then the number of lines projected onto the measured surface would increase per unit area. In other words, each line covers a smaller area and movement of these lines covers a smaller area of the measured surface. Therefore, the ability to measure h becomes more sensitive and, in turn, the ability to measure elevation change becomes more sensitive.

If the resolution of the computer's imaging system is to be increased, the computer would then measure the change in the line position more precisely and, thus measure the elevation more precisely. The sensitivity between the movement of the line and the change in elevation does not change.

If α, the angle between the imaging pathway and the projection pathway is increased, the sensitivity between the movement of the line and the change in elevation would increase, making the elevation detection more sensitive. This can be shown mathematically by determining what the quantity $\cos \beta / \sin \alpha$ would be if the angle α is increased.

If α is decreased, $\cos \beta / \sin \alpha$ increases. Thus, the same h equals a larger z, i.e., the same line displacement equals more elevational change. The ability to increase the angle is limited by the curvature of the cornea. If the angle is too large, the imaging side of the cornea will be completely shadowed by the cornea itself, and no lines will be projected onto that side of the cornea. With normal corneal curvature of 7.0 mm taken into account, the angle can be increased up to about 40 degrees with little or no problems in the efficiency of the system of the invention.

The accuracy of the measurement of the topography of the cornea is proportional to the angle of separation between the projected image and the viewing or imaging optics. As discussed hereinbefore, the viewing or imaging optics are the set of optics in apparatus 10 through which the video camera 32 views the cornea 16. The projection optics are the set of optics in apparatus 10 through which the lines are projected onto the cornea 16 or onto a measured surface. As the angle of separation between grid 36 and video camera 32 increases, so does the sine of the angle, which angle is used to determine the elevation of the surface of the cornea, making the depth represented by a one-pixel change in displacement of the grid lines smaller as already discussed herein.

Increasing the angle of separation between grid 36 and video camera 32 results in a greater number of the projected grid lines falling on the side of the cornea where projection system 34 and grid 36 are located. This tends to diminish the accuracy of the system on the total cornea. This effect is exaggerated for demonstration purposes in FIG. 9. Due to this it is not clear at this time whether a substantial change in the angle of separation is beneficial.

Increasing the number of lines projected onto the cornea could easily be done by changing the grid 36 of projection system 34 of FIG. 3. Doubling the number of the grid lines would result in an increase in the number of elevation points in the formed matrix. For example, the 2500 points of the example given hereinabove would be increased to approximately 10,000 elevation points across the corneal surface.

It has been found that occasionally the fluorescein stain disperses too rapidly, making it somewhat impossible to produce an image on the cornea. To overcome this problem, it has been found that when fluorescein is mixed with a solution of methylcellulose and artificial tears that this mixture persists long enough for the system of the invention to produce and to obtain an image of the corneal surface.

In following the teachings of the invention, quantitative measurements of curvature appear to be accurate to within about 0.10 millimeters over a wide range of curvatures for about 4.6 to 8.0 millimeters. However the deviation is greatest at both extremes of this range. For an average sized eye, with a radius of curvature of about 7.0 millimeters, it has been found by use of the invention that the accuracy is about 0.04 millimeter which is equivalent to approximately 0.3 diopters.

Preferably, the invention utilizes the optics of a Zeiss microscope with a slit lamp (FIG. 3) for projection of the grid and for the acquisition of the projected image. The video camera 32 and the projection system 34 mounted on elbows 28, 30 are used with a beam splitter 20, 22.

From the elevational information obtained by the software of the invention, curvature information of the cornea is obtained. It is to be appreciated to those skilled in the art that from the elevational information, the diopter power of the cornea can also be obtained.

The components of the invention including elbows 28, 30 adapt easily to a Zeiss or Topcon microscope. This adaptation enhances its use in an operating room in that images on the cornea are easily and quickly attainable intraoperatively without cumbersome attachments.

Also, in the invention the obtained data for the corneal surface is quickly processed and the results are instantly available. For instance, the projection system operates in approximately 1/1000th of a second and the recording system operates in approximately 1/30 of a second. In an operating room, the entire process for producing an image and obtaining the results of an image may be accomplished within about one to three minutes by the invention, whereas present techniques for obtaining the topography of a cornea may take as much as twenty to thirty minutes.

It will be appreciated, therefore, that the present invention provides an effective, quick and efficient means and method for more accurately determining the topography of a cornea of a patient in either an operating room, in an examination room or in a clinic by using rasterstereographical principles combined with an image processing unit which automatically digitizes the gridlines of a projected image through computer software. This is accomplished by causing a grid to be actually projected onto the cornea instead of the grid being reflected off the cornea which is a transparent nondiffusing member.

The system, the method, and the apparatus of the invention may be employed to derive information of the cornea of any species of the animal kingdom. Furthermore, the present invention may be used to more accurately determine the topography of any object which is transparent, nondiffusing, such as a cornea, or which is not transparent and diffusing, such as external body portions, and in some instances mandible portion where dentistry surgery is concerned. In the latter instance, it is not necessary to use the filters 38, 40, and 42, nor the fluorescein solution.

Whereas a particular embodiment of the invention has been described above for purposes of illustration, it will be evident to those skilled in the art that numerous variations of the details may be made without departing from the invention as defined in the appended claims.

We claim:

1. In a system for obtaining the topography of a cornea of an eye of a patient through a rasterstereographic technique, an apparatus comprising:
    a frame positionable generally adjacent to said eye under examination,
    light projection means carried by said frame and arranged generally in a first pathway in line with said eye for illuminating said eye,
    grid means carried by said frame and arranged in said first pathway in the same plane in line with and between said light projection means and said eye for creating a grid pattern projected onto said eye upon operation of said light projection means,
    said eye being coated with a substance capable of making said eye a nontransparent, light diffusing surface for said creating of said projected grid pattern onto said eye,
    electronic camera means carried by said frame and arranged generally in a second pathway in line with said eye and in a different positional plane from that of said grid means for obtaining and producing an image of said grid pattern projected onto said eye whereby said image of said projected grid pattern on said eye is taken directly from the surface of said eye,
    said frame having a main body portion, a centerline, and a first and second arm means each extending outwardly from and on opposite sides of said centerline of said frame,
    said first and second arm means including means for carrying said light projection means and said grid means on one side of said center line and said camera means on the other side of said centerline and whereby said first and said second pathways converge onto the surface of said eye at an angle relative to said centerline, whereby said grid is projected onto said eye at a first angle relative to said centerline and is imaged off of the surface of said eye at a second angle relative to said centerline; and
    processing means operatively connected to said electronic camera means for instantaneously obtaining data from said image of said grid pattern projected onto said eye for producing quantitative and qualitative analyses of the contour of the entire surface of said eye.

2. An apparatus of claim 1, further comprising optical means carried by said frame for focusing said grid pattern projected onto said cornea and produced by said camera.

3. An apparatus of claim 1, including said camera means being a video camera.

4. An apparatus of claim 1, including said grid means being constructed to project light and dark areas representative of light and dark grid lines.

5. An apparatus of claim 4, including said image processing means further includes means for determining the positioning and spacing of said grid lines of said image of said grid pattern.

6. An apparatus of claim 1, including said grid means being constructed of spaced-apart vertical lines whereupon light and dark vertical grid lines are projected onto said eye, and are imaged by said camera means.

7. An apparatus of claim 6, including said image processing means further comprises:
    means for selectively identifying said grid lines of said image of said grid pattern.

8. An apparatus of claim 7, including said image processing means further comprises:
    means for calculating elevation data for each said grid line of said image of said grid pattern from said data obtained from said means for identifying said grid lines of said image.

9. An apparatus of claim 8, including said means for calculating elevation data includes means using the following relationship:

$$z = (\cos\beta \times h)/\sin\alpha$$

where:
    $\alpha$ = the angle between said plane of said light projection means and said eye and said plane of said camera means and said eye,
    $\beta$ = half the value of angle $\alpha$,
    h = the change in the position of each said vertical line on said eye, and
    Z = the elevation change.

10. An apparatus of claim 8, including said image processing means further comprises:
    means for converting said elevation data into curvature data for said each grid line of said image.

11. An apparatus of claim 10, including
    said image processing means further comprises:
    means for using said curvature data for said each grid line to produce a contour plot containing a series of concentric circles representative of said topography of said eye.

12. An apparatus of claim 11, including
    said image processing means including software program means.

13. An apparatus of claim 7, including
    said means for identifying said grid lines in said image on said camera, further includes:
    means for finding an edge of each said grid line in said image by first finding a plurality of edge points for said each grid line,
    means for constructing a line segment from said plurality of edge points for said each grid line of said image, and
    means for connecting a series of said line segments to form a matrix of contiguous lines of said image.

14. An apparatus of claim 13, further comprising:
    means for determining the location of at least one reference line in said matrix of said image when said one line is projected onto said eye, including means for determining the location of the remaining lines in said matrix of said image based on said location of said reference line.

15. An apparatus of claim 14, including optical means and further comprising:
   means for correcting for any distortion in said optical means, including means for producing a calibration procedure of said grid pattern when projected onto a flat surface.

16. An apparatus of claim 15, including in said means for producing a calibration procedure,
   means for determining the deviation of said grid line according to the following relationship:

$$\text{Deviation of grid} = (\text{lines shifts} \times SP) - HD;$$

where:
   Lines shifted = the number of grid lines which are either positive or negative from said reference line to the line to be measured;
   SP = the grid spacing constant as projected onto said flat plane; and
   HD = the horizontal distance measured along a horizontal of said flat plane from said reference point to the point on the line to be measured.

17. In a system of claim 1, including said eye being coated with a fluorescein solution, and further comprising:
   first filter means interposed between said grid means and said eye for causing said fluorescein solution to fluoresce in an alternating light and dark pattern produced in said system by said grid means and said light projection means,
   second filter means interposed between said grid means and said eye in the same plane in line with said first filter means for reducing the amount of infrared transmission of the rays of said light projection means from reaching said eye, and
   third filter means interposed between said camera means and said eye for increasing the contrast of said alternating light and dark pattern.

18. An apparatus of claim 1, including said processing means being a digital computer system.

19. An apparatus of claim 1, including ocular means for at least viewing said image of said grid pattern on said eye.

20. An apparatus of claim 1, including said light projection means being a combination illuminator and flash unit.

21. An apparatus of claim 1, including said grid means being a Ronchi ruling.

22. An apparatus of claim 1, including said camera means being adapted to produce black and white images.

23. An apparatus of claim 1, including said processing means being a computer and further including software program means for said obtaining and analyzing of said data.

24. A method of obtaining the topography of a cornea of an eye of a patient through a rasterstereographic technique, the steps comprising:
   effecting an illumination on said cornea along a first pathway,
   providing grid means in said first pathway in the same plane as said illumination,
   in effecting said illumination, projecting a grid pattern of light and dark areas onto said cornea,
   coating said eye with a substance capable of making said eye a nontransparent, light diffusing surface for creating said projected grid pattern onto said eye,
   electronically obtaining an image of said areas of said grid pattern directly off of said surface of said eye along a second pathway in line with said eye and in a different positional plane from that of said grid means and said illumination,
   performing said effecting of said illumination and said projecting of said grid pattern along said first pathway at a first angle relative to an axis of said cornea of said eye and said producing of said image along said second pathway at a second angle relative to said axis of said cornea of said eye on an opposite side of said axis relative to said first angle,
   using said electronically obtained image of said projected grid pattern of said areas on said eye to obtain data, and
   processing said data of said image of said grid pattern for instantaneously producing quantitative and qualitative analyses of the contour of the entire surface of said eye.

25. A method of claim 24, including effecting a desired focusing of said eye and said grid pattern while said light and dark areas are projected onto said eye and said image is being produced.

26. A method of claim 24, including effecting said producing of said image by a video camera, and
   effecting said processing of said data of said image of said grid pattern by a computer operatively associated to said video camera.

27. A method of claim 24, including said light and dark areas being lines extending n a substantially vertical direction, and employing said method to determine the relative positioning and spacing of said lines of said image of said grid pattern.

28. A method of claim 24, including employing computer programming to effect said processing of said data.

29. A method of claim 28, including employing windows in said programming to examine a pixel in said image and determining a range of pixel intensities in said window, for ultimately locating and identifying said lines of said image.

30. A method of claim 24, including said light and dark areas being lines extending in a substantial vertical direction, and including in said processing step, selectively identifying said lines of said image of said grid pattern.

31. A method of claim 30, including employing a computer for said processing step, and algorithm means for said selectively identifying said lines.

32. A method of claim 30, including in said processing step, calculating elevation data for each said grid line of said image from said data obtained in said step for selectively identifying said lines of said image.

33. A method of claim 32, including employing a computer for said processing step, and employing algorithm means for said calculation of said elevation data.

34. A method of claim 32, including in said step of calculating said elevation data, using the following relationship:

$$Z = (\cos \beta \times h)/\sin \alpha$$

where:
   $\alpha$ = the angle between a first path created in said projecting step of said grid pattern, and a second path created in said imaging step of said grid pattern, $\beta$ = half the value of angle $\alpha$, h = the change in the position of each said line on said eye, and z = the elevation change.

35. A method of claim 32, including in said processing step, converting said elevation data into curvature data for said each line of said image.

36. A method of claim 35, including employing a computer for said processing step, and employing algorithm means for said converting of said elevation data into said curvature data.

37. A method of claim 35, including using a simplex algorithm for curve-fitting said curvature data.

38. A method of claim 35, including in said processing step, using said curvature data and producing a contour plot representative of said topography of said eye.

39. A method of claim 38, including employing a computer for said processing step, and employing algorithm means for said producing of said contour plot.

40. A method of claim 30, including in said step of selectively identifying said grid lines, further including after finding a plurality of edge points for said each grid line, finding an edge of each said grid line in said image, constructing a line segment from said plurality of edge points for said each grid line of said image, and connecting a series of said line segments to form a matrix of contiguous lines of said image.

41. A method of claim 40, including employing a computer, and algorithm means for said step of finding said plurality of edge points.

42. A method of claim 40, further including employing said method to determine the location of at least one reference line in said matrix of said image when said one line is projected onto said eye, and employing said method to determine the location of the remaining lines in said matrix of said image based on said location of said reference line.

43. A method of claim 42, including employing a computer, and algorithm means for performing said steps recited in claim 42.

44. A method of claim 40, further employing optical means and including:

correcting for any distortion in said optical means, and producing a calibration procedure for each said grid line of said pattern when projected onto a flat surface.

45. A method of claim 44, including in said method for producing a calibration procedure, determining the deviation of said each grid line by employing the following relationship:

$$\text{Deviation of grid} = (\text{lines shifted} \times SP) - HD,$$

where:

Lines shifted = the number of grid lines which are either positive or negative from said reference line to the line to be measured;

SP = the grid spacing constant as projected onto said flat plane; and

HD = the horizontal distance measured along a horizontal of said flat plane from said reference point on the line to be measured.

46. A method of claim 44, including employing a computer, and algorithm means for performing said steps recited in claim 44.

47. A method of claim 24, including the further step of applying a fluorescein solution containing a mixture of methylcellulose and artificial tears solution.

48. A method of claim 24, including the further step of applying a fluorescein solution to said eye to produce a generally light diffusing surface.

49. A method of claim 48, including the following steps for obtaining the topography of said transparent object:

causing said fluorescein solution to fluoresce in an alternating light and dark pattern produced in said projecting of said grid, reducing the amount of infrared transmission of the rays of said illumination step from reaching said object, and increasing the contrast of said alternating light and dark pattern.

50. In a system for obtaining the topography of an object through a rasterstereographic technique, comprising:

a microscope having a frame and an optical system along a centerline of said frame for viewing said object, and being positionable generally adjacent to said object for examination, said frame having a first cine elbow and a second cine elbow located opposite to each other on opposite sides of said center line, light projection means carried by said first cine elbow and arranged generally in a first optical pathway in line with said object for illuminating said object, grid means carried by said first cine elbow and arranged in said first optical pathway in line with and between said light projection means and said object for creating a grid pattern projected onto said object upon operation of said light projection means, electronic camera means carried by said second cine elbow and arranged in a second optical pathway in line with said object for instantaneously obtaining and producing an image of said grid pattern projected onto said object whereby said image of said grid pattern projected onto said object is taken directly from the surface of said object, said first cine elbow and said second cine elbow being disposed relative to said object to form an angle between said first and second optical pathways and said centerline, whereby said grid is projected onto said object at a first angle relative to said centerline and is imaged off of the surface of said object at a second angle relative to said centerline, said optical system of said microscope having a beam splitter and means for focusing and magnifying said grid pattern projected onto said object along said first optical pathway and said image of said grid pattern projected onto said object along said second optical pathway, and processing means operatively connected to said camera means for instantaneously obtaining data from said image of said grid pattern projected onto said object for producing quantitative and qualitative analysis of the contour of said object.

* * * * *

UNITED STATES PATENT AND TRADEMARK OFFICE
CERTIFICATE OF CORRECTION

PATENT NO. : 4,995,716
DATED : Feb. 26, 1991
INVENTOR(S) : Joseph W. Warnicki et al.

It is certified that error appears in the above-indentified patent and that said Letters Patent is hereby corrected as shown below:

Col. 3, line 29, a period should be inserted after "contours".
Col. 3, line 33, "a" (second occurrence) should be deleted.
Col. 4, line 39, a comma should be inserted after "object".
Col. 5, line 24, a comma should be inserted after "kingdom".
Col. 7, line 10, a comma should be inserted after "subroutine".
Col. 9, line 15, a comma should be inserted after "preferably".
Col. 9, line 63, a period should be inserted after "cornea".
Col. 15, line 59, a period should be inserted after "image".
Col. 15, line 61, a period should be inserted after "found".
Col. 18, line 49, a period should be inserted after "represented".
Claim 27, col. 24, line 32, "n" should be --in--.
Claim 49, col. 26, lines 14-15, "transparent object" should read --eye--.

Signed and Sealed this

Thirteenth Day of December, 1994

Attest:

BRUCE LEHMAN

Attesting Officer     Commissioner of Patents and Trademarks